US010328316B1

(12) United States Patent
Severa et al.

(10) Patent No.: US 10,328,316 B1
(45) Date of Patent: Jun. 25, 2019

(54) RACQUET CONFIGURED WITH INCREASED FLEXIBILITY IN MULTIPLE DIRECTIONS WITH RESPECT TO A LONGITUDINAL AXIS

(71) Applicant: WILSON SPORTING GOODS CO., Chicago, IL (US)

(72) Inventors: William D. Severa, Darien, IL (US); Dale J. Zwack, Bartlett, IL (US); Robert T. Kapheim, Chicago, IL (US); Eloisa M. Compostizo, Chicago, IL (US)

(73) Assignee: Wilson Sporting Goods Co., Chicago, IL (US)

( * ) Notice: Subject to any disclaimer, the term of this patent is extended or adjusted under 35 U.S.C. 154(b) by 0 days.

(21) Appl. No.: 16/012,283

(22) Filed: Jun. 19, 2018

Related U.S. Application Data

(60) Provisional application No. 62/641,600, filed on Mar. 12, 2018.

(51) Int. Cl.
| | |
|---|---|
| *A63B 49/02* | (2015.01) |
| *A63B 49/10* | (2015.01) |
| *A63B 49/028* | (2015.01) |
| *A63B 60/42* | (2015.01) |
| *A63B 102/02* | (2015.01) |

(52) U.S. Cl.
CPC ............ *A63B 49/028* (2015.10); *A63B 60/42* (2015.10); *A63B 2102/02* (2015.10)

(58) Field of Classification Search
CPC ............ A63B 49/00; A63B 2049/0201; A63B 2049/0203; A63B 2049/0204; A63B 49/028; A63B 49/10; A63B 60/42; A63B 2102/02
See application file for complete search history.

(56) References Cited

U.S. PATENT DOCUMENTS

| | | | |
|---|---|---|---|
| 1,828,109 A | 10/1931 | Fox | |
| 3,647,211 A | 3/1972 | Doessel et al. | |
| 3,690,658 A | 9/1972 | Howe | |
| 3,809,402 A | 5/1974 | Haines et al. | |
| 4,031,181 A * | 6/1977 | Schaefer | ................ A63B 49/08 264/135 |

(Continued)

FOREIGN PATENT DOCUMENTS

| | | |
|---|---|---|
| CH | 616849 | 4/1980 |
| EP | 0 145 820 A1 | 6/1985 |

(Continued)

*Primary Examiner* — Raleigh W Chiu
(74) *Attorney, Agent, or Firm* — Terence P. O'Brien

(57) ABSTRACT

A tennis racquet extending along a longitudinal axis and capable of being tested under a lateral bending test and a forward/rearward bending test, includes a frame having a head portion, a handle portion, and a throat portion positioned between the head and handle portions. The head portion forms a hoop that defines a string bed plane. At least the head portion and the throat portion of the racquet are formed at least in part of a fiber composite material. The throat portion includes a pair of throat elements. When the racquet is tested under the lateral bending test, the racquet has a lateral deflection of at least 6.0 mm when measured in a direction parallel to the string bed plane and perpendicular to the longitudinal axis.

23 Claims, 17 Drawing Sheets

(56) References Cited

U.S. PATENT DOCUMENTS

| | | | |
|---|---|---|---|
| 4,280,699 A | 7/1981 | Drake | |
| 4,440,392 A | 4/1984 | Popplewell | |
| 4,565,371 A | 1/1986 | Pawlicki et al. | |
| 4,583,734 A | 4/1986 | Pawlicki et al. | |
| 4,586,708 A | 5/1986 | Smith et al. | |
| 4,643,857 A | 2/1987 | Cousin et al. | |
| 4,664,380 A | 5/1987 | Kuebler | |
| 4,826,167 A | 5/1989 | Lo | |
| 4,989,870 A | 2/1991 | Janes | |
| 5,014,987 A * | 5/1991 | Soong | A63B 49/02 473/537 |
| 5,163,679 A | 11/1992 | Lo | |
| 5,176,868 A * | 1/1993 | Davis | A63B 49/10 264/257 |
| 5,232,220 A | 8/1993 | Poschenrie | |
| 5,326,097 A | 7/1994 | Yu | |
| 5,368,295 A | 11/1994 | Severa et al. | |
| 5,419,554 A | 5/1995 | Krone et al. | |
| 5,456,591 A | 10/1995 | Lo | |
| 5,507,486 A | 4/1996 | Miyamoto | |
| 5,540,877 A * | 7/1996 | Repetto | A63B 49/10 264/513 |
| 5,551,689 A | 9/1996 | Svoma et al. | |
| 5,573,242 A | 11/1996 | Yoo | |
| 5,575,875 A * | 11/1996 | Brittingham | A63B 49/10 156/175 |
| 5,580,627 A * | 12/1996 | Goodwin | A63B 49/10 428/36.3 |
| 5,897,447 A * | 4/1999 | Nishihara | A63B 49/10 473/535 |
| 5,922,255 A | 7/1999 | McLeod | |
| 5,976,742 A | 11/1999 | Sugai et al. | |
| 6,050,909 A | 4/2000 | Severa et al. | |
| 6,071,203 A | 6/2000 | Janes et al. | |
| 6,254,500 B1 * | 7/2001 | Yoneyama | A63B 49/02 473/544 |
| 6,416,432 B1 * | 7/2002 | Rosen | B32B 5/12 428/357 |
| 6,422,958 B1 * | 7/2002 | Repetto | A63B 49/10 473/536 |
| 6,500,080 B2 | 12/2002 | Severa et al. | |
| 6,524,692 B1 | 2/2003 | Rosen | |
| 6,527,656 B1 | 3/2003 | Cheng et al. | |
| 6,663,516 B2 | 12/2003 | Severa et al. | |
| 6,685,583 B2 | 2/2004 | Severa et al. | |
| 6,811,502 B1 | 11/2004 | Janes et al. | |
| 6,840,874 B2 | 1/2005 | Severa et al. | |
| 7,044,869 B2 | 5/2006 | Mauser et al. | |
| 7,140,984 B2 | 11/2006 | Mauser et al. | |
| 7,285,062 B2 | 10/2007 | McMillan et al. | |
| 7,297,080 B2 | 11/2007 | Severa et al. | |
| 7,503,860 B2 | 3/2009 | Gazzara et al. | |
| 7,867,428 B2 | 1/2011 | Filippini | |
| 7,887,444 B1 | 2/2011 | Severa et al. | |
| 7,967,706 B2 | 6/2011 | Cottey et al. | |
| 8,105,184 B2 | 1/2012 | Lammer et al. | |
| 8,323,130 B1 | 12/2012 | LeVault et al. | |
| 8,808,121 B2 | 8/2014 | Severa et al. | |
| 8,814,731 B2 | 8/2014 | Jennings | |
| 9,199,135 B2 | 1/2015 | Severa et al. | |
| 9,089,743 B2 | 7/2015 | Severa et al. | |
| D735,824 S | 8/2015 | Janes et al. | |
| 9,192,822 B2 | 11/2015 | Severa et al. | |
| 9,339,699 B2 | 5/2016 | Severa et al. | |
| 9,399,155 B2 | 7/2016 | Severa et al. | |
| 2011/0136602 A1 * | 6/2011 | Hsu | A63B 49/11 473/535 |
| 2012/0094789 A1 | 4/2012 | Lammer et al. | |
| 2012/0190473 A1 * | 7/2012 | Swist | A63B 49/02 473/282 |
| 2013/0029793 A1 | 1/2013 | Yamamoto et al. | |
| 2013/0244817 A1 * | 9/2013 | Saito | B29C 70/446 473/521 |
| 2014/0080640 A1 | 3/2014 | Lammer et al. | |
| 2015/0352410 A1 | 12/2015 | Janes et al. | |
| 2016/0271459 A1 | 9/2016 | Rocchi et al. | |
| 2016/0367875 A1 | 12/2016 | Lammer et al. | |

FOREIGN PATENT DOCUMENTS

| | | |
|---|---|---|
| EP | 0 176 021 A2 | 4/1986 |
| FR | 2509618 | 1/1983 |
| GB | 2203653 | 10/1988 |
| JP | H06 63183 A | 3/1994 |
| JP | H09 299516 A | 11/1997 |
| WO | 200990951 | 7/2009 |

* cited by examiner

RACQUET CONFIGURED WITH INCREASED FLEXIBILITY IN MULTIPLE DIRECTIONS WITH RESPECT TO A LONGITUDINAL AXIS

CROSS REFERENCE TO RELATED APPLICATION

The present application claims priority under 35 U.S.C. § 119 from U.S. Provisional Patent Application Ser. No. 62/641,600 filed on Mar. 12, 2018 by Severa et al. and entitled RACQUET CONFIGURED WITH INCREASED FLEXIBILITY IN MULTIPLE DIRECTIONS WITH RESPECT TO A LONGITUDINAL AXIS, the full disclosure of which is hereby incorporated by reference.

FIELD OF THE INVENTION

The present invention relates generally to a sports racquet. In particular, the present invention relates to racquet configured with reduced resistance to bending about a longitudinal axis of the racquet in at least a first direction that is parallel to a string bed of the racquet and a second direction that is perpendicular to the string bed of the racquet, while maintaining torsional stability.

BACKGROUND OF THE INVENTION

Sport racquets, such as tennis racquets, are well known and typically include a frame having a head portion coupled to a handle portion by a throat portion. The head portion supports a string bed having a plurality of main string segments alternately interwoven with a plurality of cross string segments.

Players generally continually seek more control, more power and/or a better feel from their racquets. Highly skilled tennis players typically seek to impart spin onto the tennis ball when impacting the ball. The ability to impart a spin (a top spin or a back spin) to a ball increases a player's ability to control the ball and to hit the ball with more power during play. For example, imparting a top spin onto a tennis ball can enable a player to swing faster, hit the tennis ball harder and still keep the tennis ball in play within the court. Imparting a top spin to a ball can enable a player to aim higher, swing faster, clear the net and keep the ball in play. Skilled tennis players also seek a racquet that provides the sense or feel of an increased "dwell time" or contact time between the racquet and the ball upon impact. The increased dwell time improves not only the responsiveness of a racquet, but also its control, including the ability to impart spin on the ball. The swing used by highly skilled tennis players to impart a top spin on to a tennis ball includes an upward sweeping motion in combination with the forward swinging motion. Such a top spin swing is more difficult to perform well than a more horizontal swing because the upward and forward motion of the head portion of the racquet during a top spin swing results in a shorter time window for impacting the ball. The upward sweeping motion of a racquet swing used to impart a top spin onto a ball also produces more of a lateral load onto the racquet during impact.

Racquets are continually designed in an effort to improve performance and playability of the racquet. Many existing racquets include high racquet frame beam heights and other racquet geometries that increase the racquet stiffness in an effort to improve the performance of the racquet. Other existing racquets incorporate a larger sized hoop portion supporting a larger sized string bed (i.e., a larger head size) in an effort to increase the size of the string bed and the racquet's performance. However, as the head size of a racquet increases, so does the polar moment of inertia of the racquet. A racquet with a higher polar moment of inertia can be more difficult to maneuver, particularly at the net or upon return of serve, than a racquet with a lower moment of inertia. Other existing racquets include designs that seek to lengthen the main and cross string segments comprising the string bed in an effort to increase the performance of the racquet. However, there continues to be a need for a racquet that further improves the performance and playability of the racquet.

There is a continuing need to provide a racquet that offers improved performance such as increased control, increased power, and/or improved feel. There is an ongoing need to provide an improved racquet design that seeks to improve all forms of racquet swing motions, including the upward sweeping motion of a topspin swing. There is a continuing need for a racquet having a string bed with an enlarged sweet spot and providing an increased "dwell time," without negatively effecting the overall performance of the racquet. It would be advantageous to provide a racquet with an enlarged sweet spot and an increased "dwell time" without increasing the polar moment of inertia of the racquet head and without negatively affecting the maneuverability of the racquet. There is also a need for a racquet having a string bed with an enlarged sweet spot that is not a radical departure in look and design from traditional sport racquet designs.

SUMMARY OF THE INVENTION

The present invention provides a tennis racquet extending along a longitudinal axis and capable of being tested under a lateral bending test and a forward/rearward bending test. The lateral bending test includes mounting the racquet in a first orientation to a first test fixture at a first longitudinal location, attaching a clamp to the racquet at a second location, operably engaging a deflection indicator to the clamp, applying a first predetermined weight to the racquet at a third location, and removing the first weight to obtain a lateral deflection measurement of the racquet with respect to the longitudinal axis. The forward/rearward bending test includes mounting the racquet in a second orientation to the first test fixture at the first longitudinal location, applying a second predetermined weight to the racquet at a fourth location, operably engaging the deflection indicator to the racquet at a fifth location, and removing the second weight to obtain a forward/rearward deflection measurement with respect to the longitudinal axis. The racquet is rotated 90 degrees about the longitudinal axis from the first orientation to the second orientation. The racquet comprises a frame including a head portion, a handle portion, and a throat portion positioned between the head portion and the handle portion. The head portion forms a hoop that defines a string bed plane. At least the head portion and the throat portion of the racquet is formed at least in part of a fiber composite material. The throat portion includes a pair of throat elements. When the racquet is tested under the lateral bending test, the racquet has a lateral deflection of at least 6.0 mm when measured in a direction that is parallel to the string bed plane and perpendicular to the longitudinal axis.

According to a principal aspect of a preferred form of the invention, when the racquet is tested under the forward/rearward bending test, the racquet has a forward/rearward deflection with respect to the longitudinal axis of at least 9.0 mm when measured in a direction that is perpendicular to the string bed plane and perpendicular to the longitudinal axis.

According to a principal aspect of a preferred form of the invention, a tennis racquet extending along a longitudinal axis and capable of being tested under a forward/rearward bending test and a torsional stability test. The forward/rearward bending test includes mounting the racquet in a first orientation to a first test fixture at a first longitudinal location, operably engaging a deflection indicator to the racquet at a second location, applying a first predetermined weight to the racquet at a third location, and removing the first predetermined weight to obtain a forward/rearward deflection measurement with respect to the longitudinal axis. The torsional stability test includes mounting the racquet to second and third test fixtures at fourth and fifth locations of the racquet, respectively, placing a second predetermined weight on an arm extending from the second test fixture to place a torsional load on to the racquet, removing the second predetermined weight to obtain an angular deflection about the longitudinal axis. The racquet comprises a frame including a head portion, a handle portion, and a throat portion positioned between the head portion and the handle portion. The head portion forms a hoop that defines a string bed plane. At least the head portion and the throat portion of the racquet is formed at least in part of a fiber composite material. The throat portion includes a pair of throat elements. When the racquet is tested under the forward/rearward bending test, the racquet has a forward/rearward deflection with respect to the longitudinal axis of at least 9.0 mm when measured in a direction that is perpendicular to the string bed plane and perpendicular to the longitudinal axis. When the racquet is tested under the torsional stability test, the racquet has an angular deflection of less than 5.5 degrees about the longitudinal axis.

According to another principal aspect of a preferred form of the invention, a tennis racquet includes a frame extending along a longitudinal axis and including a head portion, a handle portion, and a throat portion positioned between the head portion and the handle portion. The head portion forms a hoop that defines a string bed plane. The throat portion includes a pair of throat elements. At least the head portion and the throat portion of the racquet are formed at least in part of a fiber composite material. The fiber composite material includes a plurality of ply arrangements. Each of the ply arrangements includes a pair of plies with one ply having a first plurality of fibers defining a first angle with respect to a composite axis and the other ply having a second plurality of fibers defining a second angle with respect to the composite axis. The first and second angles are substantially the same except the first and second angles have opposite angular polarities with respect to the composite axis. The head portion includes at least three ply arrangements overlaying each other, and the first and second angles of at least two of the at least three ply arrangements are at least 35 degrees.

According to another principal aspect of a preferred form of the invention, a sports racquet is capable of being tested under a racquet vibration test. The racquet vibration test utilizes a modal analysis system including a hammer, an accelerometer removably attached to the racquet, and a modal analysis frame for supporting the racquet during modal analysis in a free-free condition. The racquet comprises a racquet frame extending along a longitudinal axis and including a head portion, a handle portion, and a throat portion positioned between the head portion and the handle portion. The head portion forms a hoop that defines a string bed plane. The throat portion includes a pair of throat elements. At least the head portion and the throat portion of the racquet are formed at least in part of a fiber composite material. The head portion includes a forward hoop surface and a rearward hoop surface. The distance between the forward and rearward hoop surfaces is a beam height distance. The head portion has a maximum beam height distance of at least 19 mm. When the racquet is tested under the racquet vibration test, the racquet has a vibration of no greater than 130 Hz.

This invention will become more fully understood from the following detailed description, taken in conjunction with the accompanying drawings described herein below, and wherein like reference numerals refer to like parts.

DETAILED DESCRIPTION OF THE PREFERRED IMPLEMENTATIONS

Figure 1:
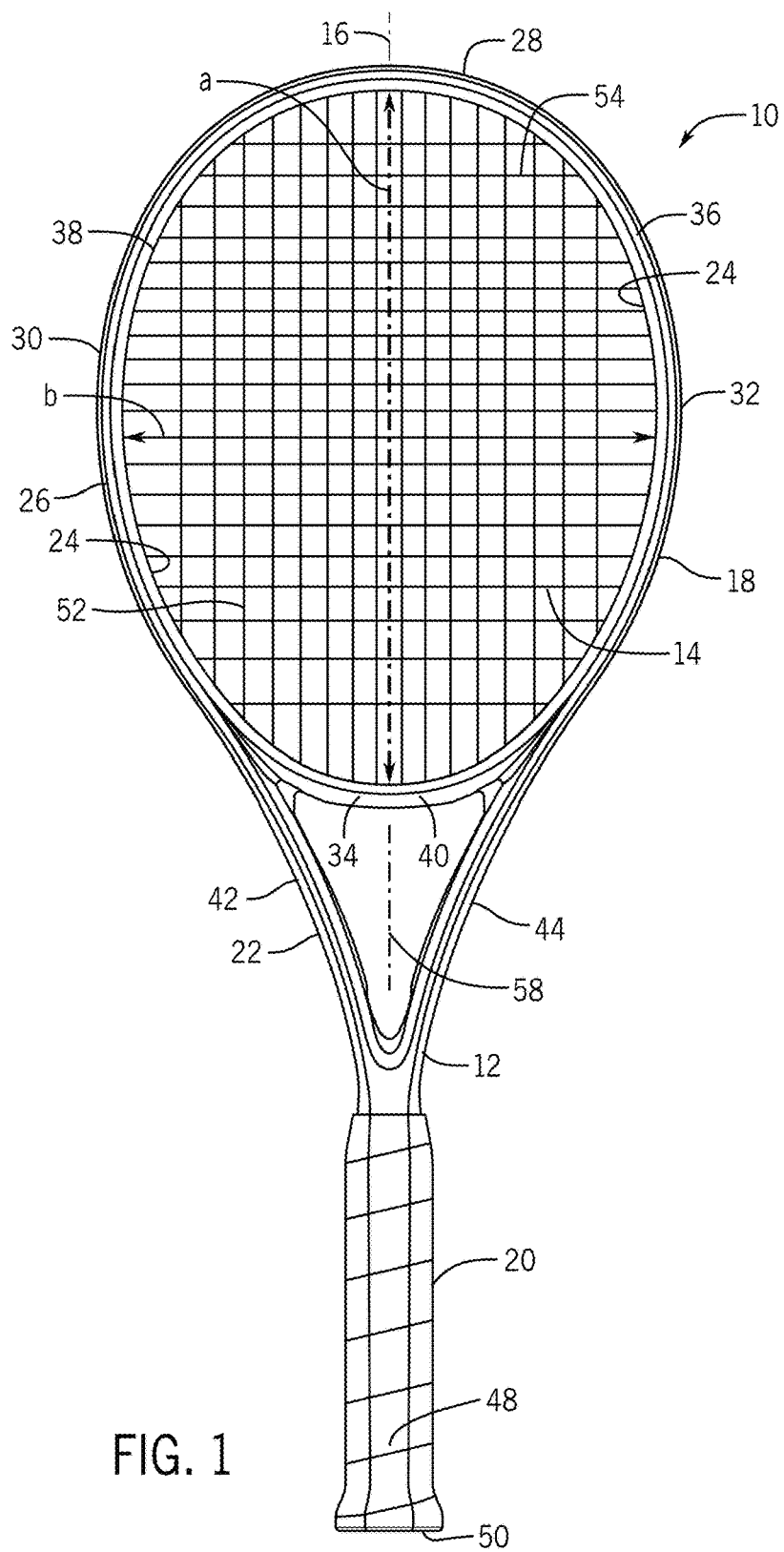
FIG. 1 is a front perspective view of a racquet in accordance with one implementation of the present invention.
Figure 2:
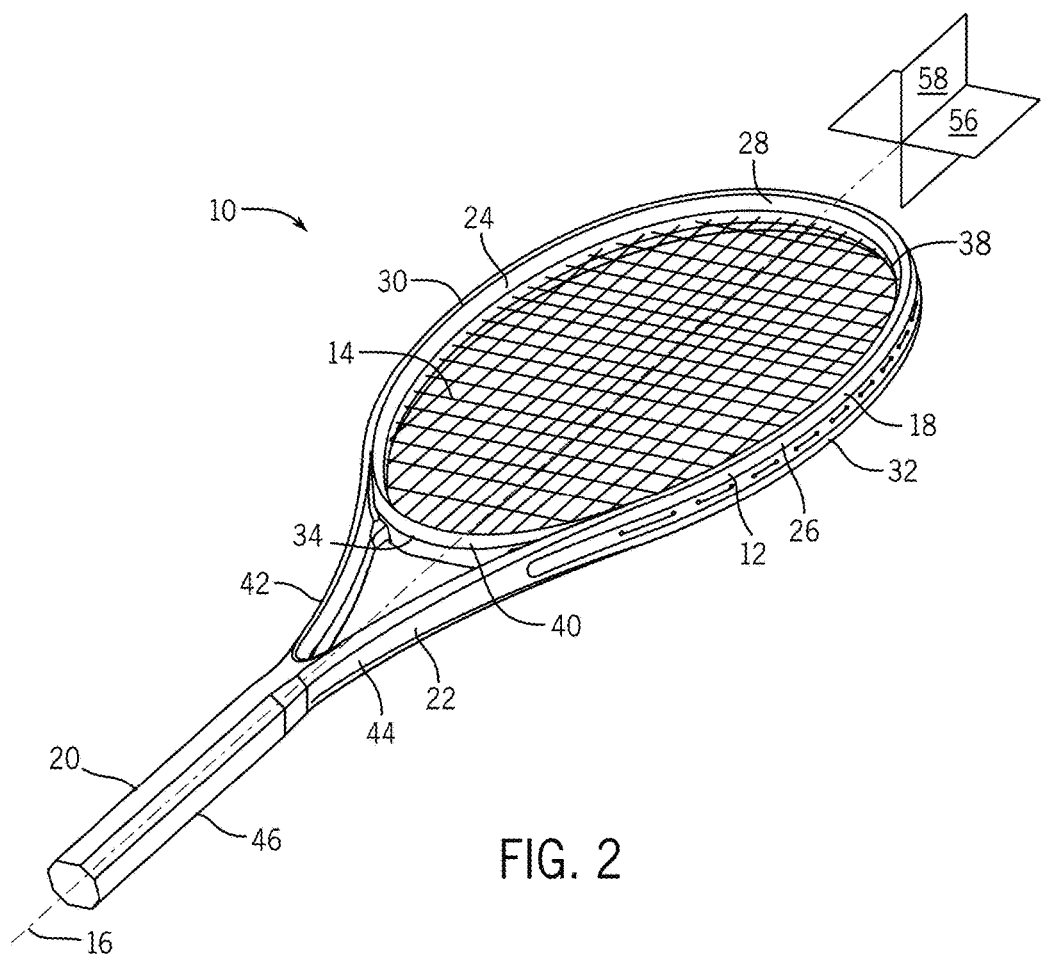
FIG. 2 is a front side perspective view of the racquet of FIG. 1 shown without a grip and without a butt cap.
Figure 3:
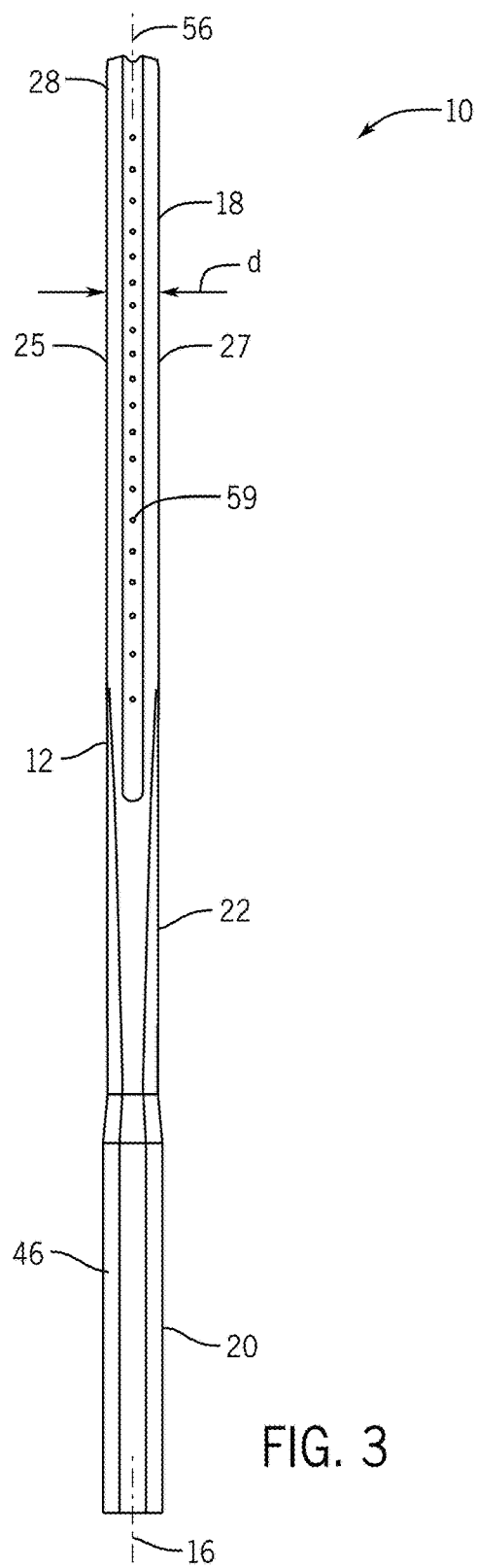
FIG. 3 is a side view of the racquet of FIG. 1.

Referring to FIGS. 1 through 3, a sports racquet is indicated generally at 10. The racquet 10 of FIG. 1 is configured as a tennis racquet. The racquet 10 includes a frame 12 extending along a longitudinal axis 16 and including a head portion 18, a handle portion 20, and a throat portion 22 coupling the head and handle portions 18 and 20. The frame 12 is a tubular structure formed of a lightweight, durable material, preferably a fiber composite material.

The head portion 18 is a tubular structure that includes inner and outer peripheral walls 24 and 26. The head portion 18 can be broken down into regions, such as, a distal region 28, first and second side regions 30 and 32, and a proximal region 34, which collectively define a hoop 36 having a string bed area 38 for receiving and supporting the string bed 14. In one preferred implementation, the proximal region 34 includes a yoke 40. The string bed area 38 is also referred to as the head size of the racquet 10. In a preferred implementation, the head size or string bed area 38 of the racquet 10 is within the range of 93 to 120 square inches. In other implementations, the head size of the racquet 10 can be within the range 98 to 115 square inches. In other implementations, other head sizes can also be used and are contemplated under the present invention. The string bed area 38 has a maximum longitudinal dimension, a, and a maximum transverse dimension, b. The hoop 36 can be any closed curved shape including, for example, a generally oval shape, a generally tear-drop shape, a generally circular, a generally pear shape, and combinations thereof. In some implementations, the maximum longitudinal dimension a can be at least 1.2 times the maximum transverse dimension b (a≥1.2*b). In other implementations, the maximum longitudinal dimension a can be at least 1.25 times the maximum transverse dimension b (a≥1.25*b). In other implementations, the maximum longitudinal dimension a can be less than 1.2 times the maximum transverse dimension b.

The yoke 40 is an elongate tubular structural member that extends from the first side region 30 to the second side region 32 of the head portion 18. In one implementation, the yoke 40 is integrally formed with the frame 12 defining the proximal region 34. For example, the yoke can be formed of a fiber composite material and molded and cured with the frame 12 of the racquet 10. In alternative preferred implementations, the yoke 40 can be connected through use of adhesives, fasteners, bonding and combinations thereof. The yoke 40 is formed of a lightweight, durable material, such as a carbon-fiber composite material. Alternatively, the yoke 40 can be formed of other materials, such as, for example, other composite materials, metallic alloys, a polymeric material, wood and combinations thereof.

In a preferred implementation, the first and second side regions 30 and 32 downwardly extend from the head portion 18 to form first and second throat tubes 42 and 44 of the throat portion 22. The first and second throat tubes 42 and 44 converge and further downwardly extend to form the handle portion 20. Accordingly, in such implementations, the frame 12 can be formed of one continuous tube of material (e.g., fiber composite material) that is curved at its middle region to form the head portion 18 then each side of the continuous tube of material can converge toward each other in the throat region 22 and the end regions of the continuous tube can be arranged side by side to form the base structure of the handle portion 20. In such implementations, the frame 12 is formed as a one piece integral structure. The handle portion 20 can further include a pallet 46, a grip 48 and a butt cap 50. In other implementations, the handle portion 20 can be a tubular structure that does not include an extension of the first and second throat tubes. In such implementations, the handle portion can be a tubular structure separate from either the throat portion or the head portion of the frame and attached to the throat portion through use of conventional fasteners, molding techniques, bonding techniques, adhesives or combinations thereof. In other implementations, the handle portion can be formed in the shape of an outer surface of a conventional pallet, thereby eliminating the need for the use of a pallet.

In other implementations, the head portion 18 can be directly connected to one or both of the throat portion 22 and the yoke 40 through the use of conventional fasteners, adhesives, mechanical bonding, thermal bonding, or other combinations thereof. In one implementation, the head portion 18 can be separated from one or both of the throat portion and the yoke by a vibration and shock absorbing material, such as an elastomer.

The racquet 10 is configured for supporting a string bed 14 and is formed by a plurality of main string segments 52 alternately interwoven or interlaced with a plurality of cross string segments 54. The string bed 14 is preferably generally uniform with constant spacing between the string segments 52 and 54. Alternatively, the string bed 14 can have some spacing variability provided that the spacing of the main and cross string segments of the string bed is most dense at the center of the string bed 14 (or near the geometric center of the string bed or string bed area). The main and cross string segments 52 and 54 can be formed from one continuous piece of racquet string, or from two or more pieces of racquet string. The racquet string is formed of a high tensile strength, flexible material. In preferred implementations, the racquet string can be formed of a polyester material, a nylon, a natural gut material and/or a synthetic gut material. The racquet string can be formed in a monofilament construction or in a multiple-filament construction, and can be formed of various different diameters (or gauges). Preferably, the diameter of the racquet string is within the range 1.10 to 1.55 mm.

The inner and outer peripheral walls 24 and 26 of the hoop 36 can include string holes 59 for receiving the racquet string. The string holes 59 can be sized to be just larger than the diameter of the racquet string, or the combination of the racquet string and a grommet, or a size that is larger to accommodate movement or deflection of the racquet string and/or grommet. The head portion 18 of the racquet 10 can also include one or more grommets or bumper guards for supporting and protecting the racquet string as it extends from one string hole to another. Additionally, the number of string holes 59 can be varied to produce different string arrangements or numbers of main string segments 52 and cross string segments 54 resulting in different string patterns. Referring to FIG. 3, the inner and outer peripheral walls 24 and 26 of the head portion 18 can define a maximum beam height distance d measured from a forward hoop surface 25 to a rearward hoop surface 27. In one implementation, the maximum beam height distance d is at least 19 mm. In other implementations, the maximum beam height distance d can be at least 20 mm. In other implementations, the maximum beam height distance d can be at least 21 mm. In still other implementations, the maximum beam height distance d can be at least 22 mm.

Referring to FIGS. 1 through 3, the main and cross string segments 52 and 54 refer to the portions of the racquet string that make up the string bed 14. The string bed 14 extends about and generally defines a string bed plane 56 (or a first plane). The string bed plane (or first plane) 56 extends through the longitudinal axis 16. A second plane 58, perpendicular to the sting bed plane (or the first plane) 56, also extends through the longitudinal axis 16. The sting bed plane 56 exists on a racquet whether it is strung or unstrung.

Conventional tennis racquets are typically formed of fiber composite material and/or aluminum, and are typically formed to be stiff structures that resist deflection about the longitudinal axis of the racquet. A stiff racquet construction is generally considered to be desirable because it is believed to improve the power and/or control of the racquet. Conventionally, the stiffness of a racquet generally refers to the racquet's resistance to bending along the longitudinal axis of the racquet and with respect to the string bed plane in a forward/rearward direction with respect to the string bed. Racquet stiffness is typically measured in a forward/rearward bending test (or a racquet stiffness test) wherein the handle portion of the racquet is fixedly secured in a test fixture with the string bed (and the string bed plane) positioned generally horizontal to the ground, a load is applied to the distal region of the head portion in a direction that is perpendicular to the string bed plane. The load causes the racquet to bend, flex or deflect with respect to the longitudinal axis and the string bed plane. The amount of deflection is measured to ascertain the stiffness level of a racquet.

High quality racquets are also typically designed to provide high levels of torsional stability. A torsionally stable racquet resists rotational movement of the head portion of the racquet upon an off-center impact with a tennis ball which improves the control of the racquet. Accordingly, conventional racquet design seeks to produce racquets with high levels of racquet stiffness and torsional stability at a predetermined racquet weight or weight range.

The shape and geometry of the head portion 18 and the throat portion 22 of the frame 12 of the racquet 10 also contributes to the racquets stiffness level and/or torsional stability. For example, racquets with high racquet beam heights are generally stiffer than racquets with lower racquet beam heights. The shape and geometry of the throat tubes 42 and 44 can also affect the stiffness of the racquet.

Contrary to conventional racquet design, the co-inventors of the present invention have identified and developed racquet constructions with decreased racquet stiffness with respect to the longitudinal axis and the string bed plane of a racquet and decreased lateral racquet stiffness with respect to the longitudinal axis and a second plane (perpendicular to the string bed plane), while maintaining desired levels of torsional stability. Contrary to conventional racquet design and expected results, the co-inventors of the present invention have discovered that racquets produced with increased longitudinal deflection along the longitudinal axis of a racquet with respect to the string bed plane and with respect to the second plane perpendicular to the string bed plane produce a significantly improved feel with improved control and/or increased power. For example, implementations of the present invention with increased flexibility with respect to the longitudinal axis 16 and the string bed plane 56 and/or the second plane 58, can improve the dwell time, control and performance of the racquet. In other implementations, with increased flexibility with respect to the longitudinal axis 16 and the second plane 58, the racquets 10 can flex in response to a lateral load, such as the lateral load that is applied to the racquet upon execution of a top spin swing. The racquets of the present invention provide a significantly better feel, and a sensation of increased interaction with the ball particularly during topspin swings which can result in better control and increased power for the player.

The co-inventors of the present invention have developed improved fiber composite racquet constructions that enable the racquet to be produced with increased levels of deflection (lower stiffness) with respect to the longitudinal axis while maintaining high levels of torsional stability.

In one implementation of the present invention, the shape and geometry of the throat tubes 42 and 44 contribute to the flexibility of the racquet 10 with respect to the string bed plane 56 and the second plane 58, while contributing to the torsional stability of the racquet 10. In another implementation of the present invention, the lay-up of the fiber composite material used to form the head portion 18 and the throat portion 22 contributes to the enhanced flexibility of the racquet 10 with respect to the string bed plane 56 and the second plane 58 while maintaining a high level of torsional stability.

As used herein, the term "fiber composite material" or "composite material" refers to a plurality of fibers within and permeated throughout a resin. The fibers can be co-axially aligned in sheets, layers or plies, or braided or weaved in sheets or layers, and/or chopped and randomly dispersed in one or more layers. A single ply typically includes hundreds or thousands of fiber bundles that are initially arranged to extend coaxially and parallel with each other through the resin that is initially uncured. Each of the fiber bundles includes a plurality of fibers. The fibers are formed of a high tensile strength material such as carbon. Alternatively, the fibers can be formed of other materials such as, for example, glass, graphite, boron, basalt, carrot, Kevlar®, Spectra®, poly-para-phenylene-2, 6-benzobisoxazole (PBO), hemp, flax, other natural fibers and combinations thereof. In one set of preferred implementations, the resin is preferably a thermosetting resin such as an epoxy or a polyester resin. In other sets of preferred implementations, the resin can be a thermoplastic resin. The composite material is typically wrapped about a mandrel and/or a comparable structure, and cured under heat and/or pressure. While curing, the resin is configured to flow and fully disperse and extend throughout the matrix of fibers. In multiple layer or ply constructions, the fibers can be aligned in different directions with respect to the longitudinal axis 16, and/or in braids or weaves from layer to layer.

Figure 4A:
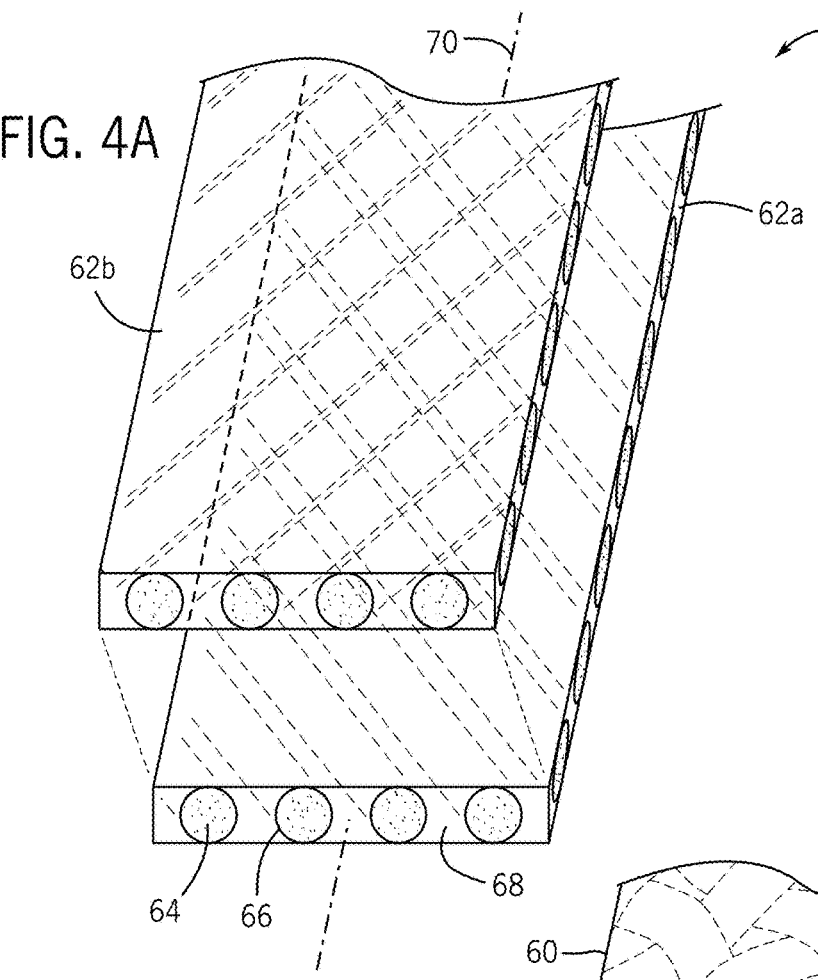
FIG. 4A is a top, side view illustrating a portion of a pair of plies of fiber composite material prior to wrapping around a bladder and a mandrel in accordance with a preferred implementation of the present invention.

Referring to FIG. 4A, a portion of a layer 60 of fiber composite material is illustrated. The layer 60 is formed by one or two plies 62 (62a and 62b) of fiber composite material. A ply 62 of fiber composite material refers to an arrangement of fibers 64 and fiber bundles 66 in a resin 68, wherein the fibers 64 and the fiber bundles 66 are arranged and aligned such that the fibers 64 and the fiber bundles 66 generally extend coaxially with respect to each other and are generally parallel to one another. The fibers 64 or fiber bundles 66 are preferably formed such that they extend along the ply 62 and form generally the same angle with respect to an axis, such as a composite axis 70. The plies 62 are typically identified, at least in part, by the size and polarity of the angle defined by the fibers 64 or fiber bundles 66 with respect to the axis 70. As shown in FIG. 4A, the ply 62a has fibers 64 and fiber bundles 66 aligned at a positive 45 degree angle ply, and the ply 62b has fibers 64 and fiber bundles 66 aligned at a negative 45 degree angle ply. In other implementations, the plies 62 can include fibers 64 or fiber bundles 66 defining a positive 30 degree angle ply, a negative 30 degree angle ply, a positive 45 degree angle ply, a negative 45 degree angle ply, a positive 40 degree angle ply, a negative 40 degree angle ply, a positive 35 degree angle ply, a negative 35 degree angle ply, a 90 degree angle ply (extending perpendicular to the axis), and a 0 degree angle ply (or extending parallel to the axis). Other positive or negative angles for plies can also be used. Accordingly, in the present application, a single ply 62 refers to a single layer of fiber composite material in which the fiber bundles 66 extend in substantially the same direction with respect to a longitudinal axis along the single layer, such as plus or positive 45 degrees or minus or negative 30 degrees. A layer 60 formed of a pair of plies 62 having fibers 64 of generally the same angle but arranged with opposite polarities is also referred to a ply arrangement. This pattern typically extends throughout a fiber composite material. The alternating angular arrangement of the fiber bundles 66 and fibers 64 is important to achieving and maintaining the structural integrity of the component or structure being formed of the fiber composite material. The overlapped region of the two plies 62a and 62b can be essential for ensuring that, once cured, the fiber composite material has the desired strength, durability, toughness and/or reliability.

Conventional fiber composite racquets are formed of fiber composite layers including plies having angular pluralities of 30 degrees or less, with the exception of a small percentage of layers having a 90 degree ply. The use of layers having plies of angular values of 30 degrees or less are used because layups including such arrangements of layers can provide the desired high levels of stiffness and also result in less manufacturing waste when preparing or cutting plies from large uncut sheets of fiber composite material. Conventional racquet design teaches away from plies having angular polarities of greater than 30 degrees because such higher angled plies would negatively affect the stiffness of the racquet and would result in unnecessary material waste that would unnecessarily increase the manufacturing cost of the racquet.

During heating/molding and curing, the resin 54 can flow between plies 62 and within the fiber bundles 66. The plies 62 preferably typically have a thickness within the range of 0.002 to 0.015 inch. In other implementations, other thickness ranges can also be used.

Figure 4B:
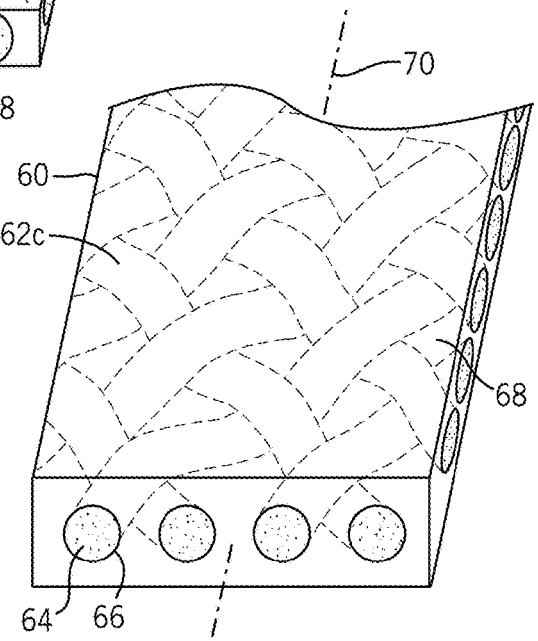
FIG. 4B is a top, side view illustrating a portion of a layer of braided fiber composite material prior to wrapping around a bladder and a mandrel in accordance with a preferred implementation of the present invention.

Referring to FIG. 4B, in other implementations, one or more of the layers 60 can include a plurality of braided fibers 62c. The braided fibers 62c can extend at angles with respect to the lay-up axis 70 of at least 35 degrees with positive and negative polarities. In other implementations, the braided fibers 62c can extend at angles with respect to the lay-up axis 70 of at least 40 degrees (with positive and negative polarities).

Figure 5:
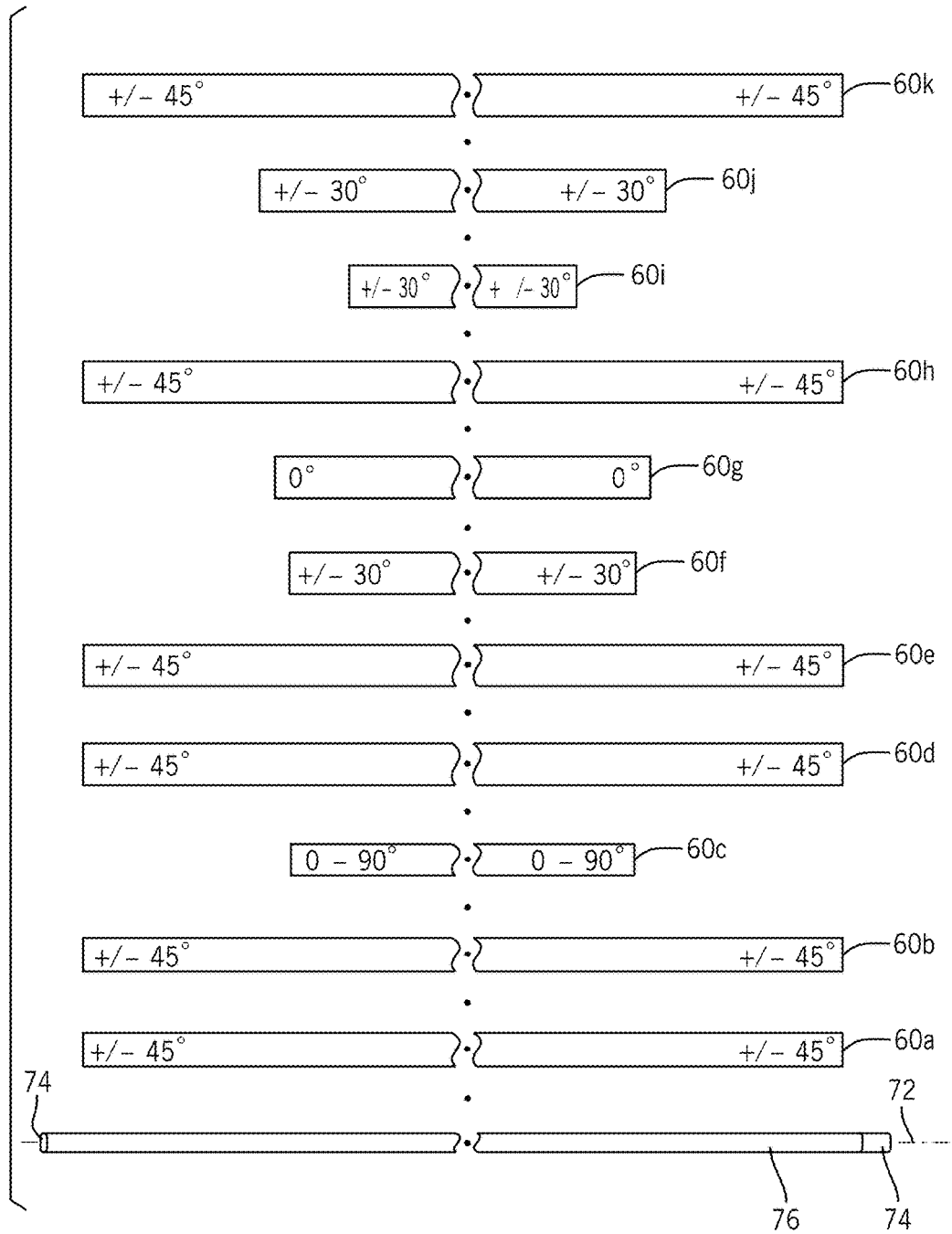
FIG. 5 is a side view of a portion of a lay-up or arrangement of layers of fiber composite material prior to molding about a bladder and a mandrel.

Referring to FIG. 5, an example arrangement of layers 60 to be wrapped or formed about a mandrel 74 is illustrated. The example arrangement of FIG. 5 is provided to demonstrate a general process of laying up a racquet frame under an example implementation of the present invention only and it is not considered to be comprehensive in any manner. Other arrangements of layers 60 including other numbers of layers, other lengths of layers, other widths of layers, other shapes of layers, other fiber angle values of layers, other sequences of layers, and combinations thereof are contemplated under the present invention. The number of plies 62 used to form a frame 12 can be within the range of 2 to 150. In a preferred implementation, the number of plies 62 used to form the frame 12, or the head portion 18 and throat portion 22 thereof, is at least 10 plies. In other implementations, other numbers of plies can be used.

The mandrel 74 is a body that is generally shaped to form the internal surface of the molded component and serves as a core upon which the layers 60 of fiber composite material can be wrapped or applied over. In one implementation, the mandrel 74 is an elongate body having a generally rectangular cross-sectional area with rounded corners. In other implementations, the mandrel can have other cross-sectional shapes. A bladder 76 is placed over, and fits around the outer surface of, the mandrel 74. Each layer 60 is wrapped or formed about a bladder 76 and mandrel 74 and follows the form or shape of the bladder 76 and mandrel 74. In the example arrangement of FIG. 5, 11 layers (layers 60a through 60k) are illustrated with layer 60a being wrapped first followed by layer 60b and so on. Importantly, a majority of the layers 60 have an angular orientation of 45 degrees (layers 60a, 60b, 60d, 60e, 60h and 60k). Each of the layers (60a, 60b, 60d through 60f, and 60h through 60k) include a pair of plies having the same angular value but with opposite polarities (e.g. 60a includes one ply having fibers extending at a positive 45 degree angle and another ply having fibers extending at a negative 45 degree angle). Further, the layers with the 45 degree angular orientation (layers 60a, 60b, 60d, 60e, 60h and 60k) form the longer layers 60 of the total number of layers in the lay-up (or plurality of ply arrangements). Accordingly, the higher angled layers generally extend along the entire length of the lay-up and therefore, when molded and cured, the higher angled layers extend over the head portion, the throat portion and the handle portion.

In other implementations, other numbers of layers 60, lengths of layers 60 and angular orientations of layers 60 can be used. In implementations of the present invention, a plurality of the layers 60 (or ply arrangements) include high angle plies, meaning plies having angles greater than or equal to 35 degrees with respect to the composite axis 70. In one implementation, at least two layers (or ply arrangements) in a lay-up 80 (see FIG. 6) of fiber composite material of at least four layers can each include at least two plies 62 having fibers extending at an angle of at least 35 degrees with respect to the composite axis 70 (a 35 degree layer or ply arrangement). In another implementation, at least two layers (or ply arrangements) in the lay-up 80 of fiber composite material of at least four layers 60 can each include at least two plies 62 having fibers extending at an angle of at least 40 degrees with respect to the composite axis 70 (a 40 degree layer or ply arrangement). In another implementation, at least two layers (or ply arrangements) 60 in a lay-up 80 of at least four layers can each include at least two plies 62 having fibers extending at an angle of at least 45 degrees with respect to the composite axis 70 (a 45 degree layer or ply arrangement). In other implementations, a lay-up 80 of fiber composite material (or plurality of ply arrangements) of at least four layers 60 can include at least three layers 60 being at least 35 degree layers. In another implementation, a lay-up 80 of at least four layers 60 can include at least three layers 60 being at least 40 degree layers. In another implementation, a lay-up of fiber composite material (or plurality of ply arrangements) of at least four layers 60 can include at least three layers 60 being at least 45 degree layers.

In other implementations, the lay-up 80, or plurality of ply arrangements, can include at least five layers 60, at least six layers 60, at least seven layers 60 and higher. In such lay-ups, the number of layers 60 being at least 35 degree angles can be at least three layers, or four layers, or five layers or more layers. In other implementations, the lay-up 80 or plurality of ply arrangements can include at least five layers 60, at least six layers 60, at least seven layers 60 and higher, and the number of layers 60 being at least 40 degree angles can be at least three layers, or four layers, or five layers or more layers. In still other implementations, the lay-up 80 or plurality of ply arrangements can include at least five layers 60, at least six layers 60, at least seven layers 60 and higher, and the number of layers 60 being at least 45 degree angles can be at least three layers, or four layers, or five layers or more layers.

In preferred implementations, the length of the high angle layers (at least 35 degree angle layers, at least 40 degree angle layers, or at least 45 degree angle layers) extend over at least 40 percent of the total length of the lay-up the head portion 18 of the racquet 10. In other implementations, the length of the high angle layers extend over at least 50 percent of the total length of the lay-up the head portion 18 of the racquet 10. In other implementations, the length of the high angle layers extend over at least 70 percent of the total length of the lay-up the head portion 18 of the racquet 10. In preferred implementations, the length of the layers 60 or ply arrangements can be sufficiently long such that, when molded and cured, the high angle layers (at least 35 degree angle layers, at least 40 degree angle layers, or at least 45 degree angle layers) extend over at least the head portion 18 of the racquet 10. In other implementations, the length of the layers 60 or ply arrangements can be sufficiently long such that, when molded and cured, the high angle layers (at least 35 degree angle layers, at least 40 degree angle layers, or at least 45 degree angle layers) extend over at least the head portion 18 and the throat portion 22 of the racquet 10.

In one implementation, at least 50 percent of the layers 60 of a lay-up or plurality of ply arrangements can be formed with carbon fibers. In another implementation, at least 75 percent of the layers 60 in a lay-up or ply arrangement can be formed of carbon fibers. In one implementation, each of the high angle layers (at least 35 degree angle layers, at least 40 degree angle layers, or at least 45 degree angle layers) in the lay-up 80 include a resin and have a fiber area weight of at least 100 g/m$^2$. In another implementation, each of the high angle layers (at least 35 degree angle layers, at least 40 degree angle layers, at least 45 degree angle layers, or at least 60 degrees) in the lay-up 80 include a resin and have a fiber area weight of at least 120 g/m$^2$.

Figure 6:
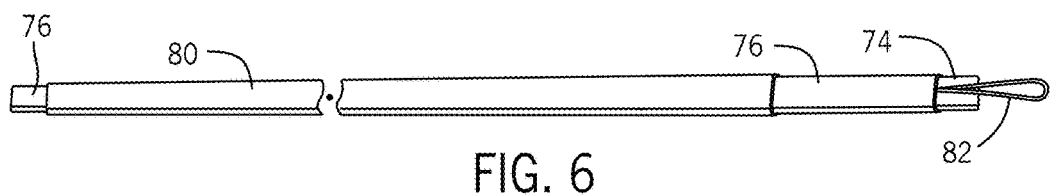
FIG. 6 is top side perspective view of the lay-up of layers of fiber composite material of FIG. 5 with the mandrel and the bladder.

Referring to FIG. 6, when the layers 60 are wrapped or laid up around the bladder 76 and the mandrel 74, the plies 62 are no longer arranged in a flat sheet, and therefore, the fiber bundles 66 and fibers 64 no longer follow or define generally parallel lines. Rather, the fiber bundles 66 and fibers 64 are adjacent to one another, and are curved or otherwise formed so that they follow substantially the same adjacent paths. For example, when the ply 62 is wrapped about the bladder 76 and the mandrel 74, the ply 62 can take a generally cylindrical or tubular shape and the fiber bundles 66 and fibers 64 can follow the same cylindrical path or define a helical path (depending upon their angle within the ply 62). The fibers 64 remain adjacent to one another, are aligned with each other and follow substantially similar paths that are essentially parallel (or even co-axial) for example, when viewed in a sectional view in a single plane or other small finite segment of the ply 62.

In one implementation, the mandrel 74 may include a pull tab 82 for facilitating the pulling or removal of the mandrel 74 from the plurality of layers 60 wrapped about the bladder 76 and the mandrel 74. The lay-up 80 of FIG. 6 is uncured. In one implementation, the mandrel 74 using the pull tab 82 can be drawn, pulled or otherwise removed from the bladder and the lay-up 80.

Figure 7:
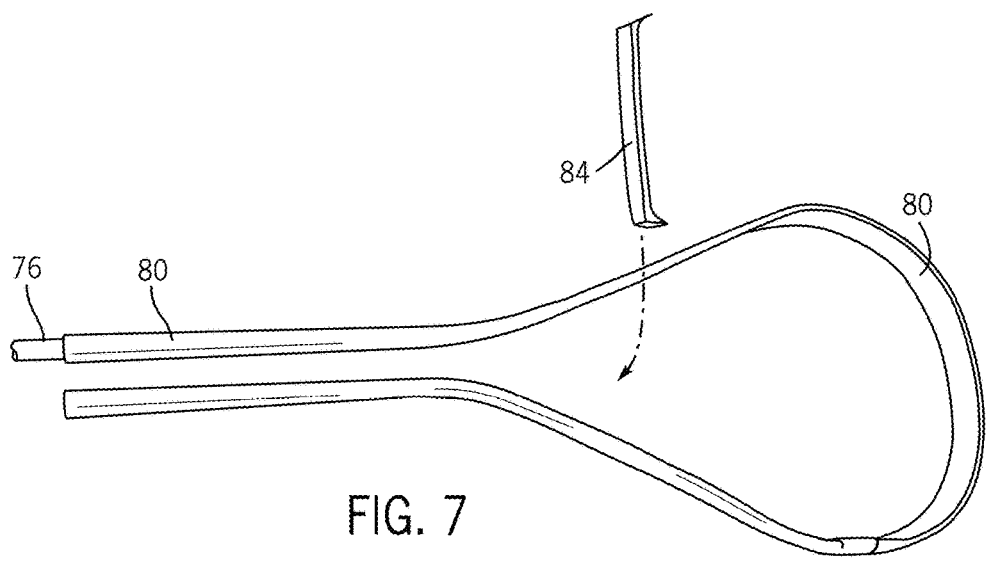
FIG. 7 is top side perspective view of the lay-up of layers of fiber composite material of FIG. 6 with the mandrel removed and the lay-up of layers curved to approximate the shape of a racquet, and a yoke fiber composite lay-up.
Figure 8:
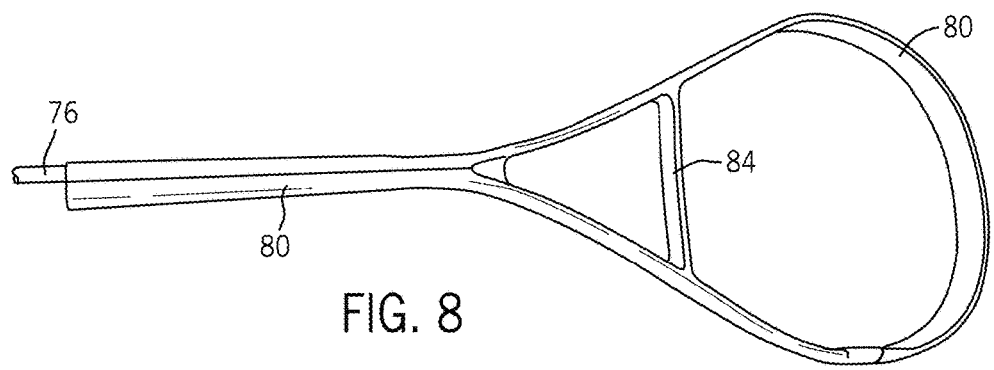
FIG. 8 is a top side perspective view of the lay-up of layers of fiber composite material of FIG. 7 prior to being placed into a racquet forming mold.

Referring to FIGS. 7 and 8, once the mandrel 74 is removed from the bladder 76 and the lay-up 80, the uncured lay-up 80 can be gently positioned into the shape of a racquet frame. An uncured yoke lay-up 84 of fiber composite material can be prepared for positioning next to the curved lay-up 80. As shown in FIG. 8, the lay-up can be shaped to resemble a racquet frame, and the yoke lay-up 84 can be attached to the lay-up 80. In one implementation, additional relatively short ties or tying plies can be applied over the connection points of the yoke lay-up 84 to the lay-up 80. In other implementations, the yoke lay-up may be replaced with a preformed yoke structure that is added attached to the lay-up 80 prior to molding.

Figure 9:
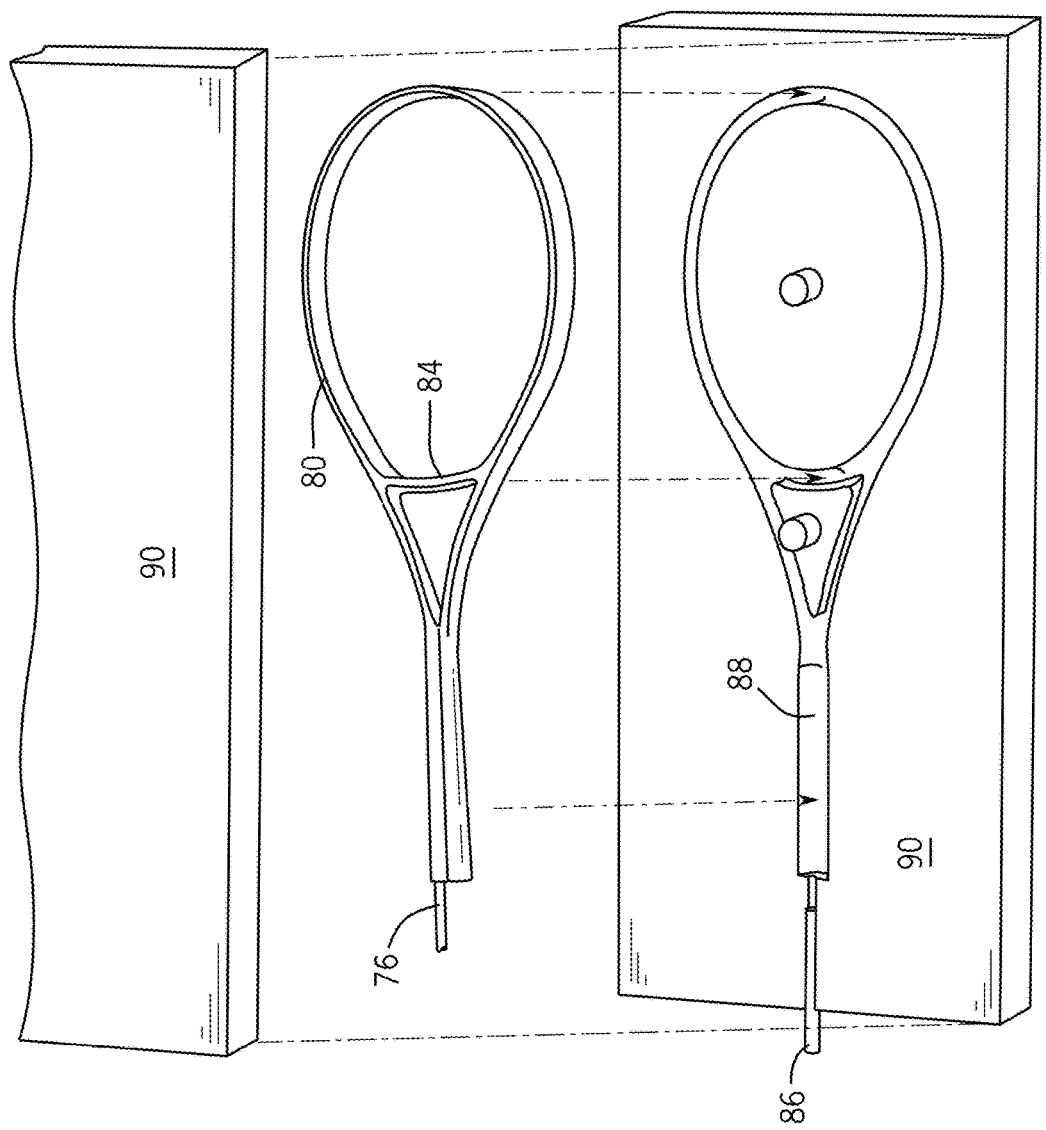
FIG. 9 is a top side exploded view of the lay-up of layers of fiber material being placed into a racquet forming mold.

Referring to FIG. 9, the uncured lay-up 80 and the uncured yoke lay-up 84 is positioned within a mold cavity 88 of a racquet forming mold 90. A supply line 86 can be attached to the bladder 76 for supplying air or other gas to the bladder, and the pieces of the racquet forming mold 90 can be positioned around the lay-up 80 and the yoke lay-up 84. The bladder 76 can be pressurized by air or other gas to a predetermined pressure, and the racquet forming mold 90 can then be heated in an oven or furnace to a predetermined temperature. Once subjected to heat and pressure, the viscosity of the resin 68 in the lay-up 80 and the yoke lay-up 84 drops and the resin 68 flows through out the plies 62 of the lay-up 80 and yoke lay-up 84 in the mold cavity 88 creating a more uniform structure and the fibers 64 are positioned into the shape of the mold cavity. After a first predetermined amount of time, the racquet forming mold 90 is removed from the heat and the lay-up 80 and yoke lay-up 84 are allowed to cool. After a second predetermined amount of time, the racquet forming mold 90 is opened and the racquet frame 12 is removed from the mold 90. The frame 12 of the racquet 10 can have a weight within the range of 260 gm to 355 gm. In other implementations, the frame of the racquet can have a weight outside of the 180 gm to 370 gm range.

The incorporation of high angle layers 60 (at least 35 degree angle layers, at least 40 degree angle layers, at least 45 degree angle layers, or at least 60 degree angle layers) into the lay-up 80 of the frame 12 of the tennis racquet 10 provides unique combination of performance characteristics that unexpectedly and significantly improve the feel and playability of the racquet. The incorporation of high angle layers 60 into the lay-up 80 of the frame 12 of the tennis racquet 10 can result in the racquet 10 having a high amount of deflection in a forward/rearward racquet stiffness test, a high amount of deflection in a lateral racquet stiffness test, while maintaining a high level of torsional stability under a racquet torsional stability test. Accordingly, racquets built in accordance with implementations of the present invention can exhibit low or reduced longitudinal stiffness with respect the longitudinal axis 14, the string bed plane 56 and the second plane 58, while maintaining a desirable amount of torsional stability. This combination of attributes is unique to racquet construction and results in racquets having exceptional feel, playability, control and/or power.

Racquets built in accordance with the present invention can provide a number of significant advantages to users of the racquets. Characteristics such as, (1) racquet deflection measured with respect to the longitudinal axis of the racquet in a forward/rearward direction with respect to the string bed plane 56, and (2) racquet deflection measured with respect to the longitudinal axis of the racquet in a lateral direction with respect the second plane 58 can be substantially increased through use of racquets built in accordance with the present invention. Additionally, racquets built in accordance with the present invention exhibit desirable levels of torsional stability, and exceptionally low frequency values which improve the feel of the racquet. Further, racquets built in accordance with the present invention exhibit relatively low vibration levels contributing to improved feel of such racquets.

Racquets built in accordance with the present invention, when tested in a racquet lateral bending test, can provide a lateral deflection of at least 6.0 mm when measured in a direction that is parallel to the string bed plane and perpendicular to the longitudinal axis. Accordingly, racquets built in accordance with the present invention have a reduced resistance to bending with respect to the longitudinal axis in a direction parallel to the string bed plane and perpendicular to the longitudinal axis. In other implementations, a racquet built in accordance with the present invention, when tested in a racquet lateral bending test, can provide a lateral deflection of at least 6.5 mm when measured in a direction that is parallel to the string bed plane and perpendicular to the longitudinal axis. Additionally, in other implementations, a racquet built in accordance with the present invention, when tested in a racquet lateral bending test, can provide a lateral deflection of at least 7.0 mm when measured in a direction that is parallel to the string bed plane and perpendicular to the longitudinal axis.

Racquets built in accordance with the present invention, when tested in a racquet forward/rearward bending test, can provide a forward/rearward deflection of at least 9.0 mm when measured in a direction that is perpendicular to the string bed plane and perpendicular to the longitudinal axis. Accordingly, racquets built in accordance with the present invention have a reduced resistance to bending with respect to the longitudinal axis in a direction perpendicular to the string bed plane and perpendicular to the longitudinal axis. In other implementations, a racquet built in accordance with the present invention, when tested in a racquet forward/rearward bending test, can provide a forward/rearward deflection of at least 10.0 mm when measured in a direction that is perpendicular to the string bed plane and perpendicular to the longitudinal axis. In other implementations, a racquet built in accordance with the present invention, when tested in a racquet forward/rearward bending test, can provide a forward/rearward deflection of at least 10.5 mm when measured in a direction that is perpendicular to the string bed plane and perpendicular to the longitudinal axis. Additionally, in other implementations, a racquet built in accordance with the present invention, when tested in a racquet forward/rearward bending test, can provide a forward/rearward deflection of at least 11.0 mm when measured in a direction that is perpendicular to the string bed plane and perpendicular to the longitudinal axis.

Racquets built in accordance with the present invention, when tested in a racquet torsional stability test, can also provide an angular deflection of less than 5.5 degrees. In other implementations, a racquet built in accordance with the present invention, when tested in a racquet torsional stability test, can provide an angular deflection of no more than 5.0 degrees.

Still further, racquets built in accordance with the present invention can provide frequency values from modal analysis of no greater than 135 Hz. In other implementations, racquets built in accordance with the present invention can provide frequency values from modal analysis of no greater than 130 Hz. In other implementations, racquets built in accordance with the present invention can provide frequency values from modal analysis of no greater than 120 Hz. In still other implementations, racquets built in accordance with the present invention can provide frequency values from modal analysis of no greater than 115 Hz.

Figure 10:
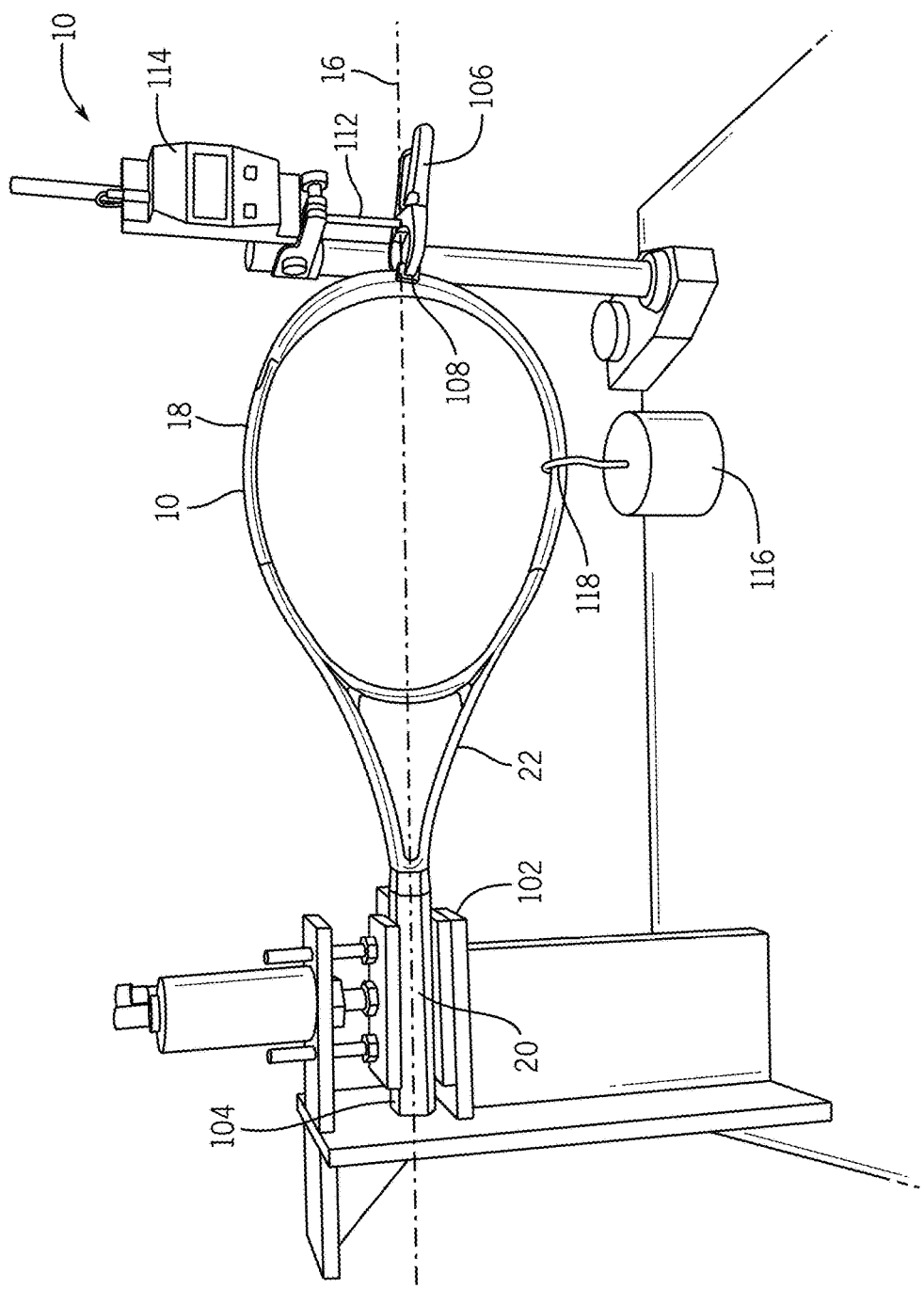
FIG. 10 is a side perspective view of a racquet lateral bending test assembly and an unstrung racquet undergoing a racquet lateral bending test with a first weight applied to the racquet.
Figure 11:
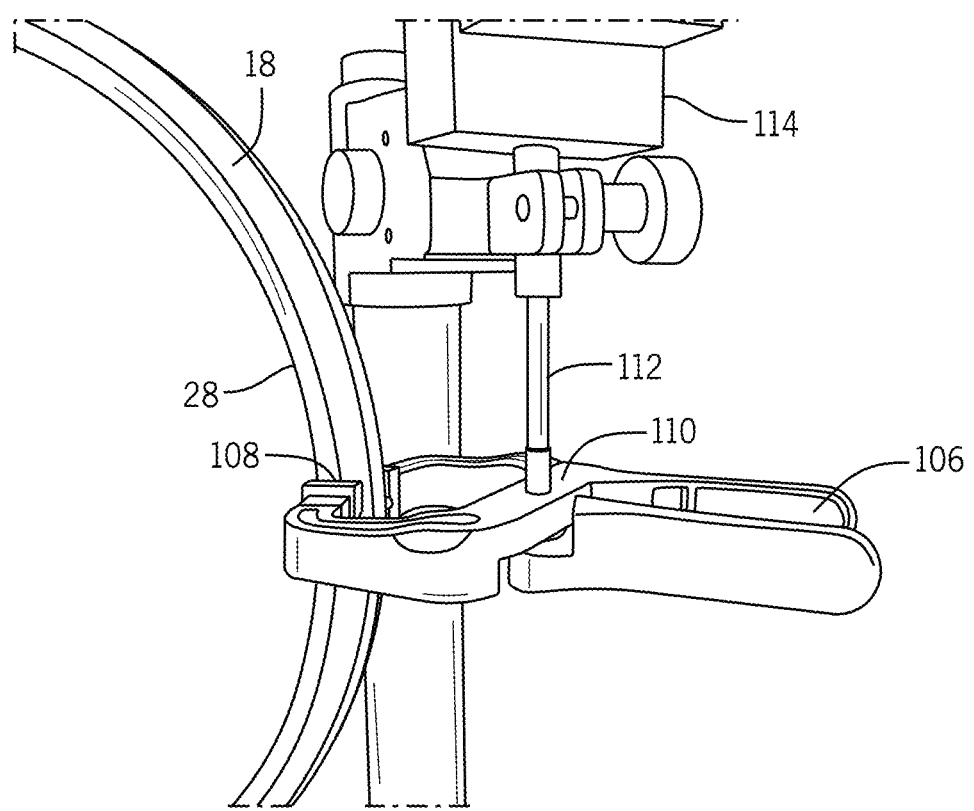
FIG. 11 is a top, side perspective view of a clamp removably attached to a distal region of a head portion of the racquet and a deflection meter engaging the clamp under the racquet lateral bending test assembly of FIG. 10.
Figure 12:
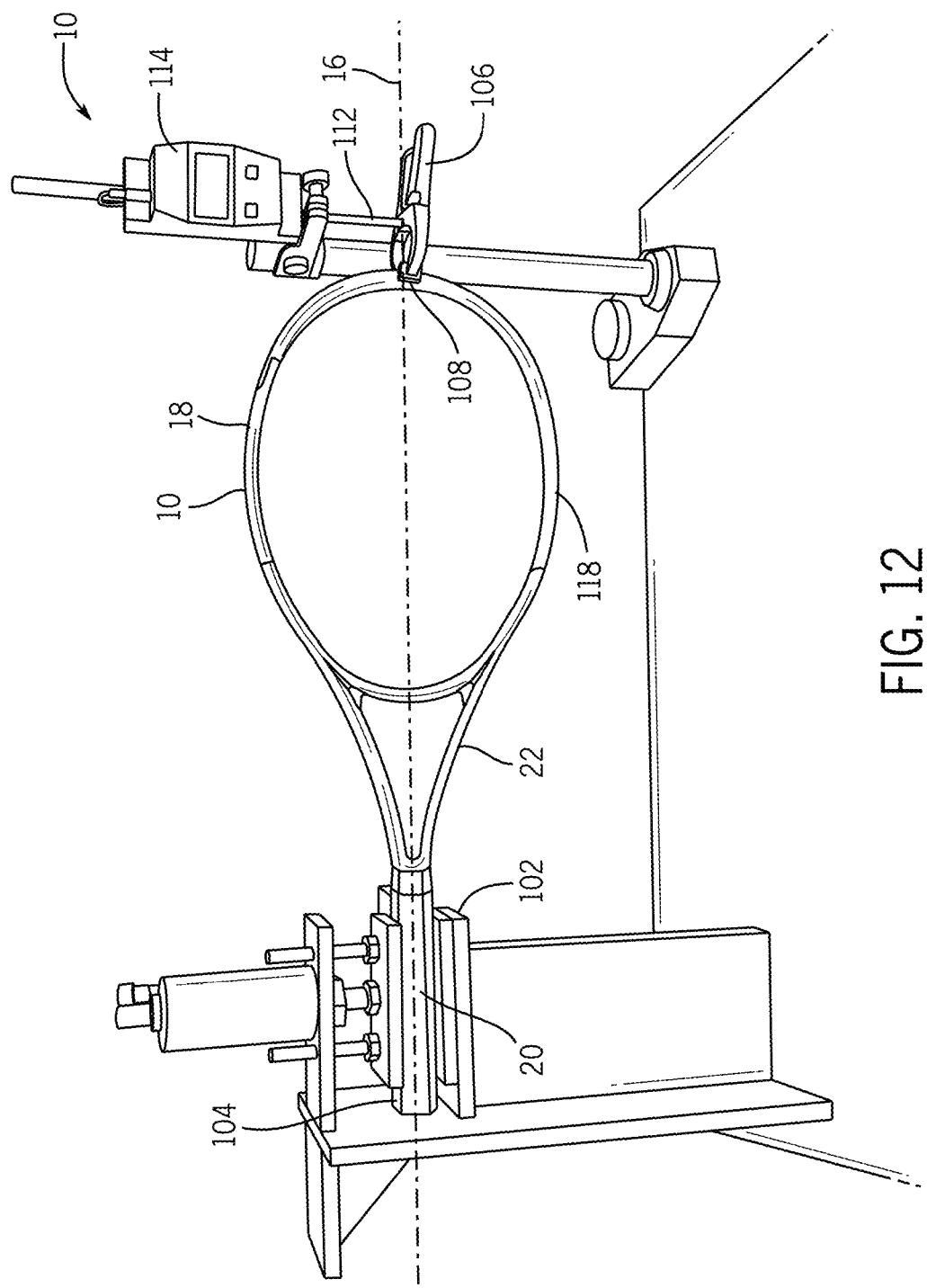
FIG. 12 is a side perspective view of the racquet lateral bending test assembly of FIG. 10 with the first weight removed from the racquet.

Referring to FIGS. 10 through 12, Wilson Sporting Goods Co. conducted a racquet lateral bending test using a racquet deflection test assembly 100. The racquet lateral bending test measures the lateral flexibility of a racquet, or a racquet's resistance to bending with respect to the longitudinal axis 16 of the racquet and the second plane 58. The term "racquet lateral bending test" means a test meeting the following description. The string bed, the grip and the butt cap are removed from the handle portion of the racquet. Under the racquet lateral bending test, the handle portion of the racquet is securely mounted to a first test fixture 102 at a first location 104 in a first orientation, in which the longitudinal axis 16 of the racquet 10 is parallel to the ground and the string plane 56 of the racquet 10 is perpendicular to the ground. In one implementation, the first test fixture 102 can be a pneumatic clamp. In other implementations other forms of test fixtures can be used. Referring to FIGS. 10 and 11, a test clamp 106 is releasably, fixedly secured to the racquet 10 at a second location 108, which is at the distal end region 28 of the head portion 18 of the racquet 10 at a 12 o'clock position of the hoop 36. The test clamp 106 is a light weight clamp having a weight of less than 50 grams, and includes a horizontally positioned side surface 110 for operably engaging a sensing probe 112 of a digital deflection indicator 114, such as a Digimatic™ Indicator Model ID-150ME by Mitutoyo of Aurora, Ill. The location where the sensing probe 112 of the digital deflection indicator 114 engages the side surface 110 is positioned 40 mm from a distal end surface (at the 12 o'clock position) of the distal end region 28 of the head portion 18. A first weight 116 is applied to a third location 118 of the racquet 10. The third location 118 is positioned on the second side region 32 of the head portion 18 generally at the 3 o'clock position of the hoop 36 at a distance that is 20 inches from a proximal end of the racquet 10 along the longitudinal axis 16 of the racquet 10. The first weight 116 is a 3 kg weight, which, when applied to the racquet at the third location 118, causes the racquet 10 to deflect with respect to the longitudinal axis 16. The sensing probe 112 is positioned to engage the side surface 110 of the clamp 106, and the digital deflection indicator 114 is zeroed. Referring to FIG. 12, the first weight 116 is removed from the racquet 10 and a lateral deflection measurement is taken from the digital defection indicator 114. Although the racquet shown in FIGS. 10-12 is unstrung and although the racquet lateral bending test can also be performed on a strung racquet, for purposes of the claimed invention, the racquet tested under the racquet lateral bending test is unstrung.

Figure 13:
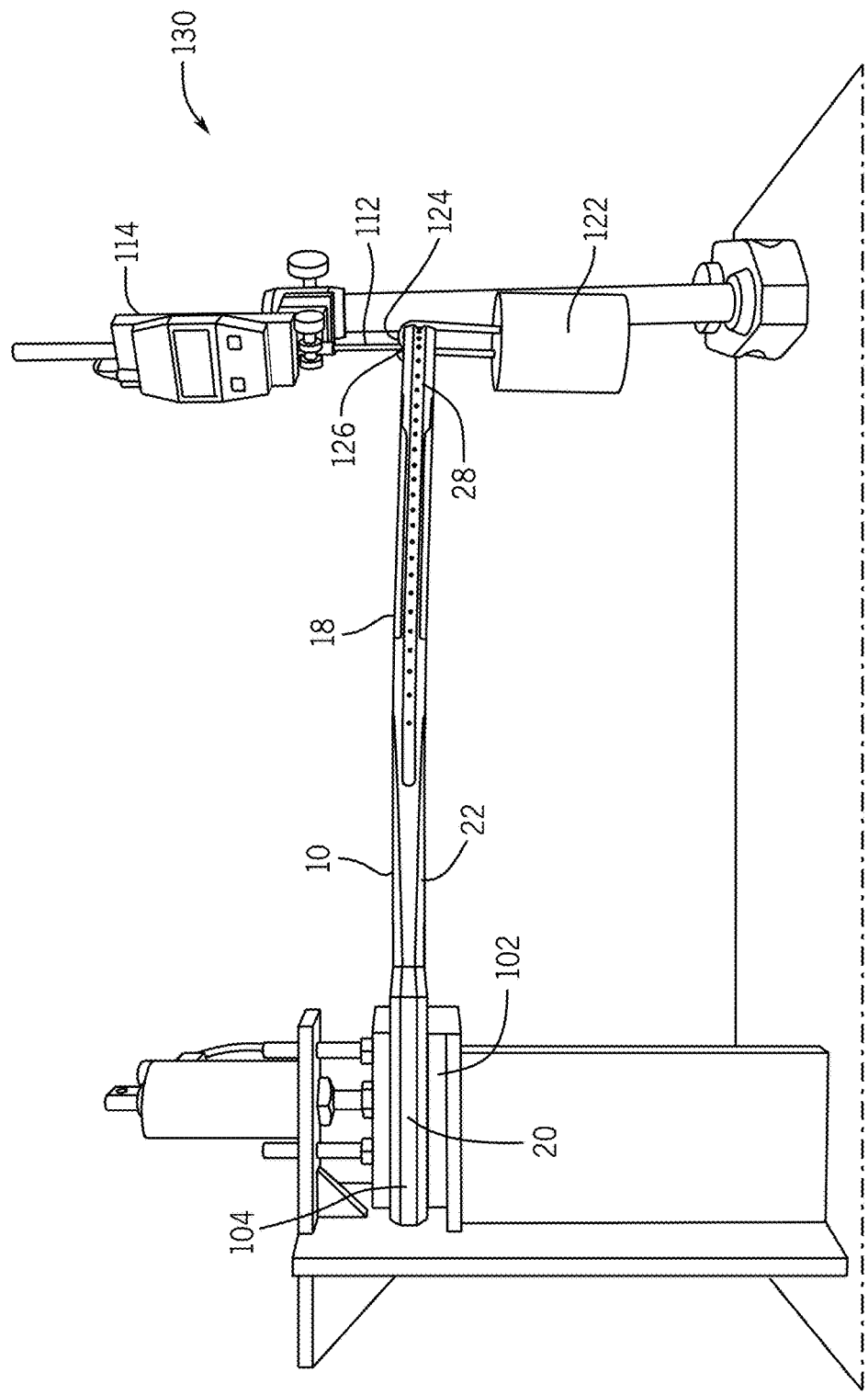
FIG. 13 is a side perspective view of a racquet forward/rearward bending test assembly and a racquet undergoing a racquet forward/rearward bending test with a second weight applied to a distal region of a head portion of the racquet.
Figure 14:
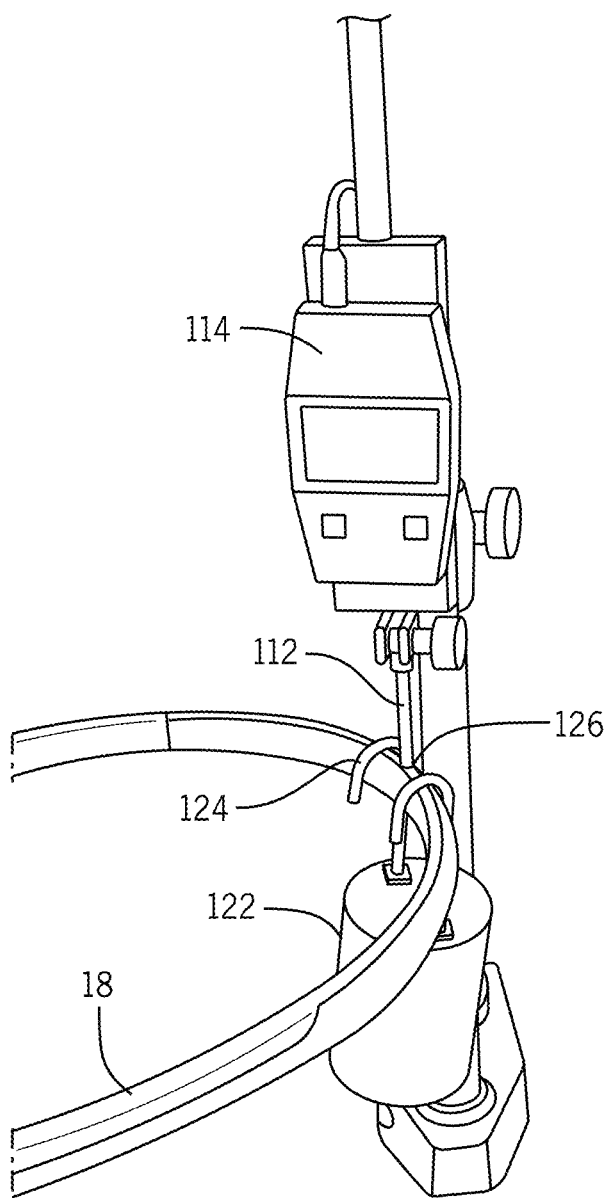
FIG. 14 is a top, side perspective view of a deflection meter and a second weight applied to the racquet under the racquet forward/rearward bending test assembly of FIG. 13.
Figure 15:
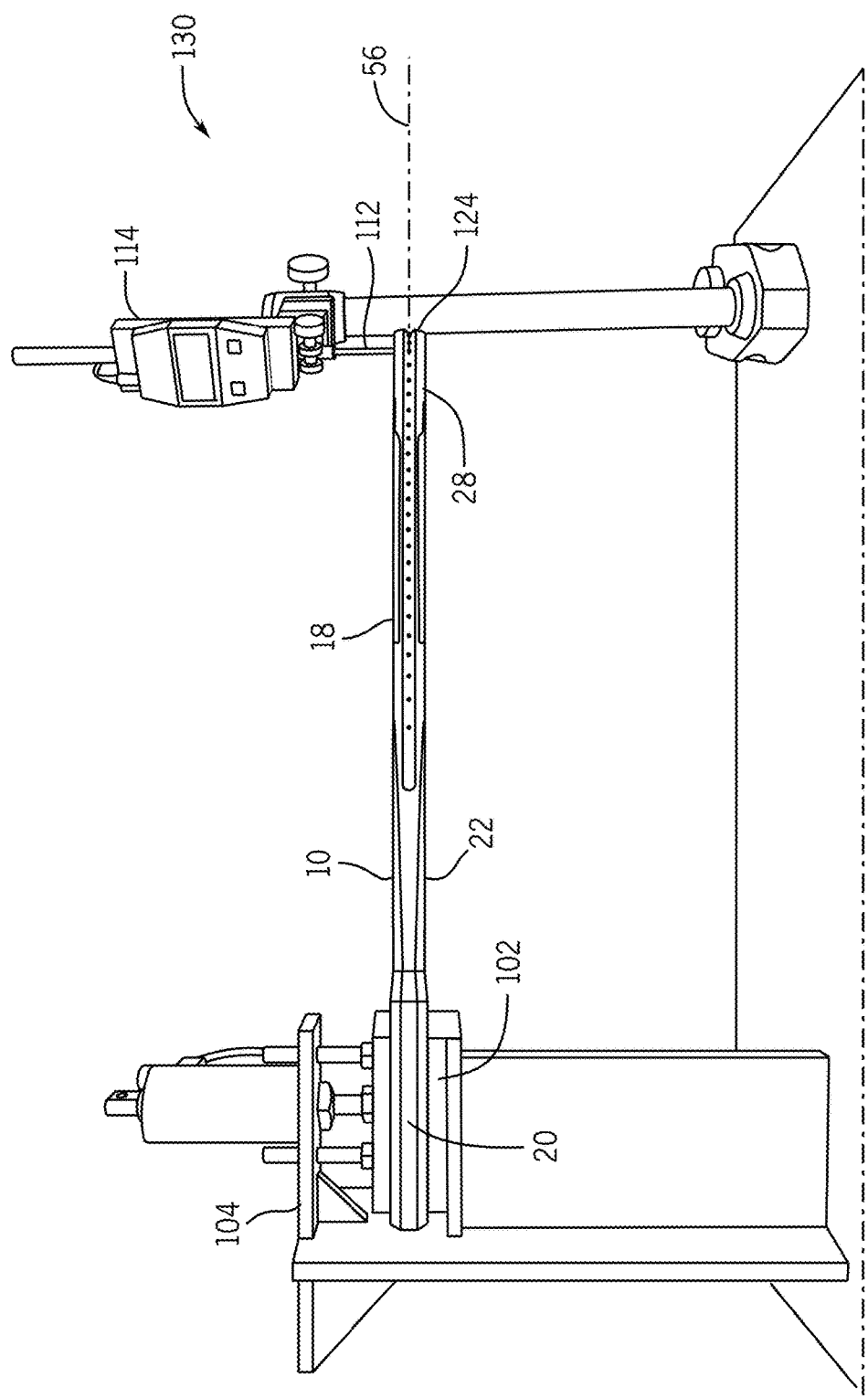
FIG. 15 is a side view of the racquet forward/rearward bending test of FIG. 13 with the second weight removed from the racquet.

Referring to FIGS. 13 through 15, Wilson Sporting Goods Co. conducted a racquet forward/rearward bending test (also referred to as a racquet stiffness test or a racquet stiffness index test) using a racquet forward/rearward bending test assembly 130. The racquet forward/rearward bending test measures the flexibility of a racquet in a forward/rearward direction with respect to the sting bed plane 56, or a racquet's resistance to bending with respect to the longitudinal axis 16 of the racquet and the string bed plane 56. The term "racquet forward/rearward bending test" means a test meeting the following description. The string bed, the grip and the butt cap are removed from the handle portion of the racquet 10. Referring to FIGS. 13 and 14, under the racquet forward/rearward bending test, the handle portion 20 of the racquet 10 is securely mounted to the first test fixture 102 at the first location 104 in a second orientation, in which the longitudinal axis 16 of the racquet 10 is parallel to the ground and the string bed plane 56 of the racquet 10 is also parallel to the ground. In other words, the racquet 10 is rotated 90 degrees about the longitudinal axis 16 from the first orientation to the second orientation. A second weight 122 is applied to a fourth location 124 of the racquet 10. The fourth location 124 being the distal end region 28 of the head portion 18 of the racquet 10 at approximately a 12 o'clock position of the hoop 36. The sensing probe 112 of the digital deflection indicator 114, such as a Digimatic™ Indicator Model ID-150ME by Mitutoyo of Aurora, Ill. at a fifth location 126, which is at the top side of the distal end region 28 of the head portion 18 of the racquet 10 at the 12 o'clock position. The second weight 122 is a 2.8 kg weight, which, when applied to the racquet at the fourth location 124, causes the racquet 10 to deflect with respect to the longitudinal axis 16 and the string bed plane 54. The sensing probe 112 is positioned to engage top side of the distal end region 28 of the head portion 18 at a fifth location 126, and the digital deflection indicator 114 is zeroed. Referring to FIG. 15, the second weight 122 is removed from the racquet 10 and a racquet deflection measurement is taken from the digital defection indicator 114. The term "forward/rearward" is meant to refer to deflection of the racquet in either direction that is perpendicular from the original string bed plane 56 and the longitudinal axis 16 of the racquet. In the forward/rearward racquet bending test, the application of the second weight to the distal end of the head portion of the racquet causes the racquet to deflect downward in a rearward direction. Then, when the second weight is removed, the racquet moves upward in a forward direction. The total amount of the forward movement is the deflection measurement (or the stiffness value of the racquet). Although the racquet shown in FIGS. 13-15 is unstrung and although the racquet forward/rearward bending test can also be performed on a strung racquet, for purposes of the claimed invention, the racquet tested under the racquet forward/rearward bending test is unstrung.

Figure 16:
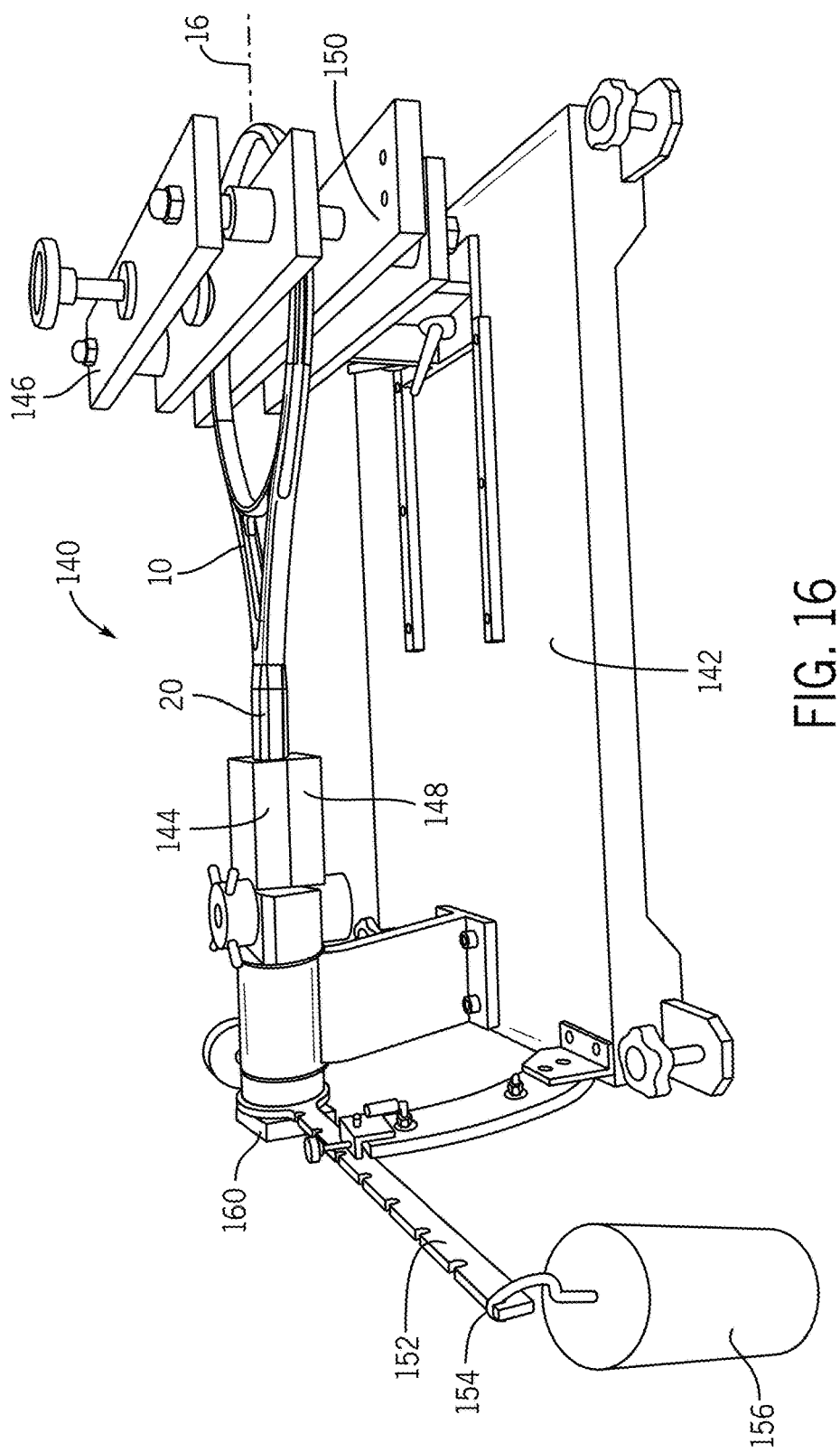
FIG. 16 is a top, side perspective view of a racquet torsional stability test assembly and a racquet undergoing a racquet torsional stability test with a third weight applied to the racquet torsional stability assembly.
Figure 17:
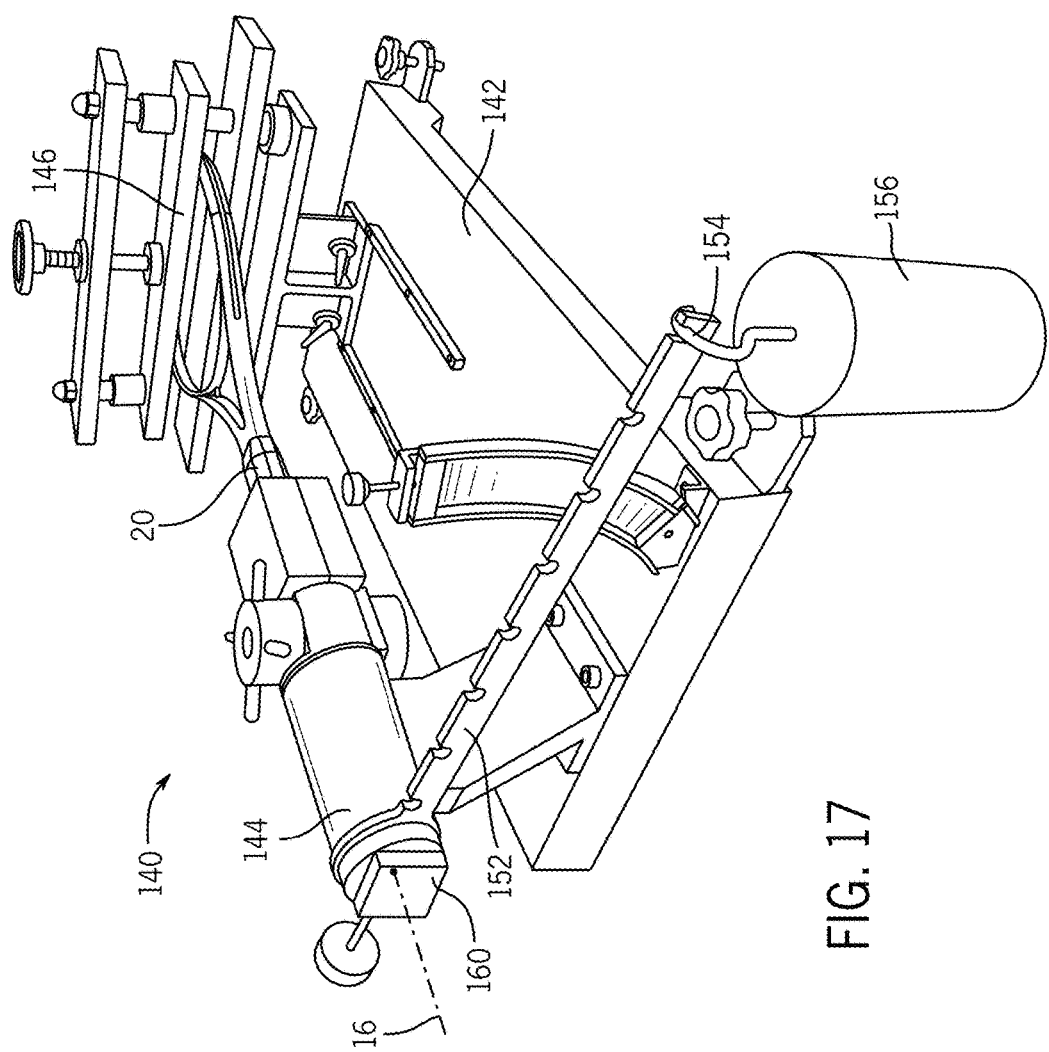
FIG. 17 is a first end, side perspective view of the racquet torsional stability test assembly of FIG. 16.
Figure 18:
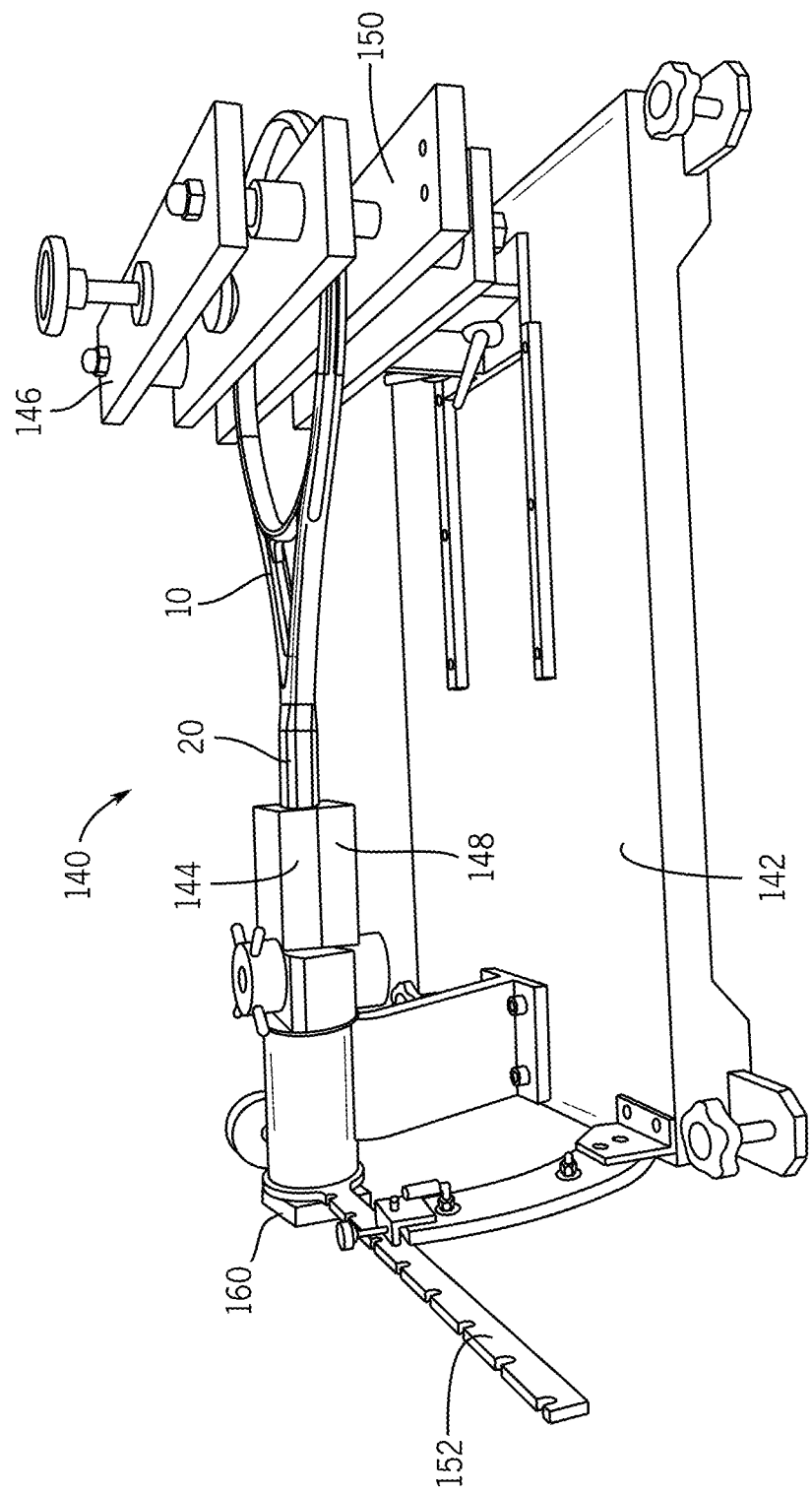
FIG. 18 is a top, side perspective view of the racquet torsional stability test assembly and the racquet undergoing a racquet torsional stability test of FIG. 16 with the third weight removed from the racquet torsional stability assembly.
Figure 19:
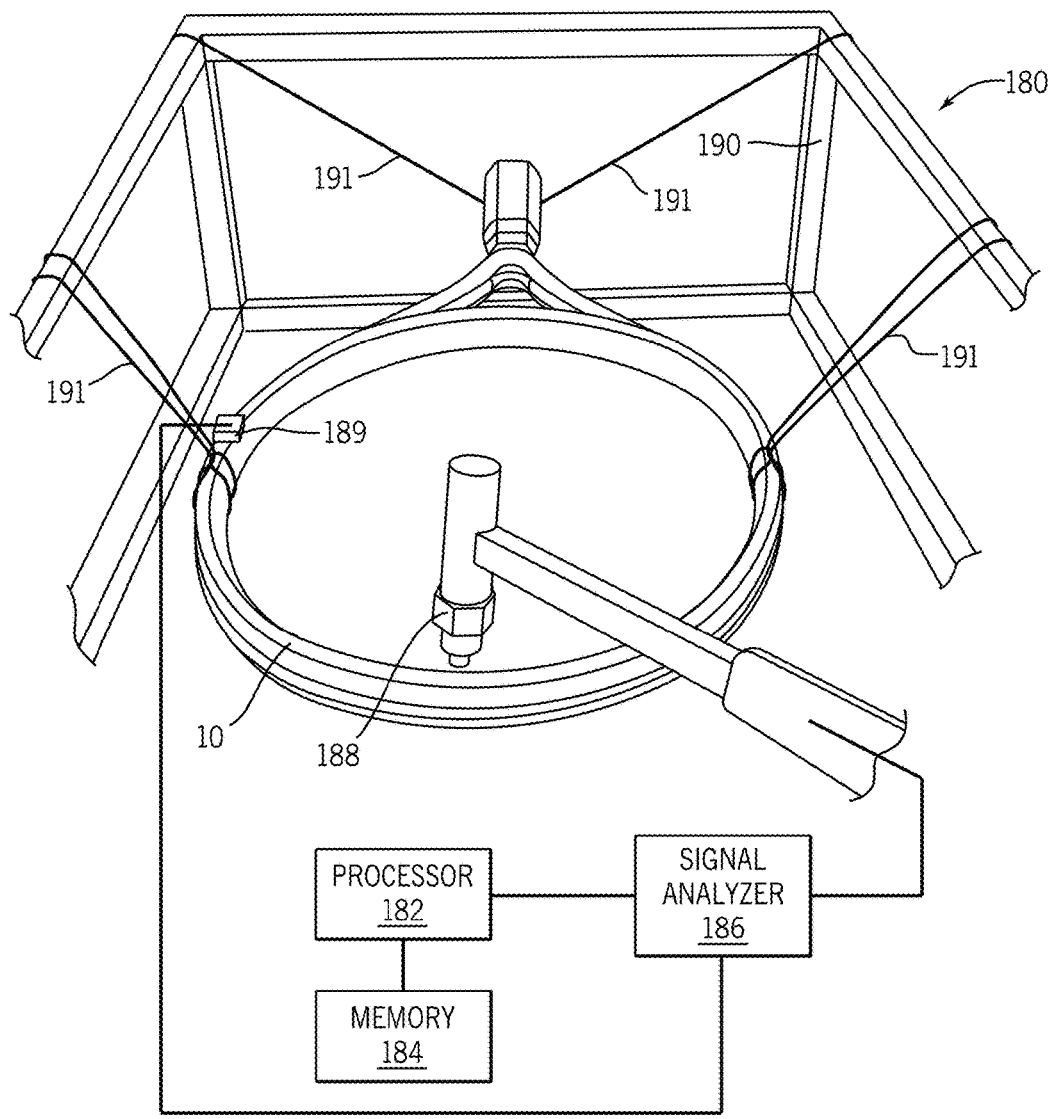
FIG. 19 is a top, end perspective view of a vibration analysis test being performed on a racquet.

Referring to FIGS. 16 through 18, Wilson Sporting Goods Co. also conducted a racquet torsional stability test using a racquet torsional stability test assembly 140. The racquet torsional stability test includes a frame 142 with second and third test fixtures 144 and 146 for mounting the racquet 10 to at sixth and seventh locations 148 and 150 of the racquet 10, respectively. The term "racquet torsional stability test" means a test meeting the following description. The string bed, the grip and the butt cap are removed from the handle portion 20 of the racquet 10. The racquet 10 is positioned in the second and third test fixtures 144 and 146 with the longitudinal axis 16 and string bed plane 54 of the racquet 10 parallel to the ground. The second test fixture 144 fixedly secures the handle portion 20, and is pivotally mounted to the frame 142 to allow for pivotal or rotational movement of the second fixture 144 (and the handle portion 20 clamped to the second fixture 144) about the longitudinal axis 16 of the racquet 10. The second test fixture 144 further includes an arm 152 that radially projects or extends from the second test fixture 144 and the longitudinally axis 16. The arm 152 includes one or more indexes 154 for receiving a third weight 156 at a predetermined distance from the longitudinal axis 16. In one implementation, the third weight is a 6.9 kg weight and the predetermined distance is 40 cm from the longitudinal axis 16. The third test fixture 146 fixedly secures the head portion 18 of the racquet 10 in a fixed position with the string bed plane 56 of the racquet 10 positioned parallel to the ground. A digital inclinometer 160, such as a Wixey™ Digital Angle Gauge, Model No. WR300, Type 2, by Barry Wixey Development of Sanibel, Fla., is removably mounted to the second test fixture 144 at the longitudinal axis 16. The third weight 156 is applied to the arm 152 at the predetermined distance of 40 cm from the axis 16. The third weight 156 applied to the arm 152 places a torsional load onto the handle portion 20 of the racquet 10 and causes rotation of the second test fixture 144 (and the handle portion 20) with respect to the frame 142 and about the longitudinal axis 16. Referring to FIG. 18, the digital inclinometer 160 is zeroed, and the third weight 156 is removed. The angular deflection or movement of the arm 152 and the handle portion 20 with respect to the longitudinal axis 16 is measured. Although the racquet shown in FIGS. 16-18 is unstrung and although the racquet torsional stability test can also be performed on a strung racquet, for purposes of the claimed invention, the racquet tested under the racquet torsional stability test is unstrung.

The advantages of the present invention were illustrated by performance of the racquet lateral bending test, the racquet forward/rearward bending test and the racquet torsional stability test on racquets made in accordance with implementations of the present invention and on several existing racquet models. Table 1 below lists the results of the racquet lateral bending test, the racquet forward/rearward bending test and the racquet torsional stability test on a total of twenty two racquets, 3 of the racquets being prototypes of the present invention, and 19 existing, prior art racquet models. All of the racquets were tested unstrung.

TABLE 1

| normal bending | mm | lateral bending | mm | torsion | degrees |
| --- | --- | --- | --- | --- | --- |
| Flex Prototype 2 | 12.1 | Flex Prototype 1 | 10.5 | Wilson Profile | 2.0 |
| Flex Prototype 1 | 12.1 | Flex Prototype 2 | 7.7 | Wilson Profile Comp | 2.8 |
| Flex Prototype 3 | 11.2 | Flex Prototype 3 | 7.0 | Wilson Ultra 2 | 3.1 |
| Prince Tour 100 | 7.7 | Prince Tour 100 | 5.7 | Wilson Hammer 6.2 | 3.1 |
| Wilson Aggressor | 7.7 | Wilson PS 5.5 SI | 5.6 | Wilson Galaxy | 3.4 |
| Head Prestige Pro | 7.5 | Head Radical Tour | 5.4 | Wilson Ultra 2 mp | 3.5 |
| Head Radical Tour | 7.4 | Head Prestige Pro | 5.2 | Wilson Ultra 85 | 3.6 |
| Wilson Sting | 6.5 | Head Radical mp | 5.0 | Babolat Pure Drive | 3.8 |
| Wilson Ultra 2 | 6.5 | Wilson Blade 98 | 4.7 | Flex Prototype 3 | 3.9 |
| Head Radical mp | 6.5 | Babolat Aero | 4.5 | Wilson PS 5.5 SI | 4.3 |
| Prince Graphite mp | 6.4 | Wilson Hammer 6.2 | 4.2 | Head Radical Tour | 4.8 |
| Wilson Blade 98 | 6.2 | Wilson Galaxy | 3.8 | Babolat Aero | 4.8 |
| Wilson PS 5.5 SI | 5.9 | Prince Graphite mp | 3.7 | Flex Prototype 1 | 4.9 |
| Babolat Aero | 5.5 | Wilson Profile Comp | 3.7 | Flex Prototype 2 | 4.9 |

TABLE 1-continued

| normal bending | mm | lateral bending | mm | torsion | degrees |
|---|---|---|---|---|---|
| Wilson Ultra 100 | 5.3 | Wilson Ultra 2 mp | 3.6 | Wilson Sting | 4.9 |
| Babolat Pure Drive | 5.2 | Wilson Ultra 2 | 3.6 | Wilson Blade 98 | 4.9 |
| Wilson Ultra 85 | 5.1 | Wilson Ultra 85 | 3.5 | Head Radical mp | 5.2 |
| Wilson Hammer 6.2 | 5.1 | Babolat Pure Drive | 3.5 | Head Prestige Pro | 5.4 |
| Wilson Galaxy | 4.7 | Wilson Sting | 3.3 | Wilson Aggressor | 5.5 |
| Wilson Profile Comp | 4.1 | Wilson Ultra 100 | 3.2 | Prince Graphite mp | 5.8 |
| Wilson Ultra 2 mp | 3.9 | Wilson Aggressor | 3.1 | Prince Tour 100 | 6.2 |
| Wilson Profile | 3 | Wilson Profile | 3.1 | Wilson Ultra 100 | 6.2 |

The existing, prior art racquets include several older racquet models and several current racquet models, all of which are formed at least in part of fiber composite material. The older racquet models tested included the following racquets: Wilson® Profile®; Wilson® Profile® Comp™, Wilson® Ultra® 2; Wilson® Ultra® 2 MP; Wilson® Ultra® 85; Wilson® Ultra® 100; Wilson® Galaxy™; Wilson® Hammer® 6.2; Wilson® ProStaff® 5.5 SI; Wilson® Sting™; Wilson® Aggressor® and Prince® Graphite MP. The Wilson® branded racquet models were produced from Wilson Sporting Goods Co. of Chicago, Ill. from the years 1980 to 2018. The Prince® Graphite MP racquet was produced in 1983 by ABG-Prince OPCO, LLC of New York, N.Y. The current prior art racquet models tested included the following racquets: Wilson® Blade® 98; Babolat® Pure Drive™; Babolat® Aero™; Head® Radical® Tour™; Head® Radical® MP and Prince® Tour™ 100. The Babolat® branded racquets were produced by Babolat VS of Lyon, France. The Head® branded racquets were produced by HEAD Sport GmbH of Kennelbach, Austria.

The three prototype racquets built in accordance with implementations of the present invention are referred to as the Flex Prototype 1, the Flex Prototype 3 and the Flex Prototype 2. The three prototypes include frames of fiber composite material including several 45 degree layers. The three Flex Prototype racquets are all 27 inches in length. The head size or string bed area 38 of each of the Flex Prototype 1 and Flex Prototype 3 racquets was 102 sq. inches, and the head size of the Flex Prototype 2 racquet was 98 sq. inches.

All three prototype racquets exhibited exceptionally high lateral bending in the racquet lateral bending test compared to existing, prior art racquets. All three prototype racquets demonstrated a lateral deflection of at least 6.0 mm, at least 6.5 mm, and at least 7.0 mm. The lowest lateral deflection reading of the three prototype flex racquets (the Flex Prototype 3) was over 22 percent greater than the highest lateral deflection value of the 19 existing, prior art racquet models. The other two prototype flex prototype racquets, Flex Prototype 2 and Flex Prototype 1, exhibited lateral deflections of 7.7 mm and 10.5 mm, respectively, which are more than 35 percent and 84 percent greater than the highest lateral deflection value of the 19 existing, prior art racquet models, respectively. Additionally, the average lateral deflection measurement of the three flex prototype racquets (8.4 mm) was more than twice the average lateral deflection measurement of the 19 prior art racquets (4.1 mm) from the racquet lateral bending test.

All three prototype racquets also exhibited exceptionally high forward/rearward deflection readings, or bending, in the racquet forward/rearward bending test compared to existing, prior art racquets. All three prototype racquets demonstrated a forward/rearward deflection of at least 8.0 mm, at least 8.5 mm, at least 9.0 mm, at least 9.5 mm, at least 10.0 mm, at least 10.5 mm and at least 11.0 mm. The lowest forward/rearward deflection reading of the three prototype flex racquets (the Flex Prototype 3) was over 45 percent greater than the highest forward/rearward deflection value of the 19 existing, prior art racquet models. The other two prototype flex prototype racquets, Flex Prototype 2 and Flex Prototype 1, each exhibited forward/rearward deflections of 12.1 mm, which is more than 57 percent greater than the highest forward/rearward deflection value of the 19 existing, prior art racquet models, respectively. Additionally, the average forward/rearward deflection measurement of the three flex prototype racquets (11.8 mm) was more than twice the average forward/rearward deflection measurement of the 19 prior art racquets (5.7 mm) from the racquet forward/rearward bending test.

The results of testing the three prototype flex racquets and 19 existing prior art racquet under the racquet torsional stability test demonstrates that despite the exceptionally and uniquely high lateral bending flexibility and high forward/rearward bending flexibility, the prototype racquets maintain a high level of torsional stability. Under implementations of the present invention, racquets can provide unprecedented levels of lateral flexibility and forward/rearward flexibility while maintaining a desirable level of torsional stability. Therefore, racquets built in accordance with the present invention provide exceptional feel, with increased levels of control, particularly for players who impart spin onto the ball during play, while maintaining a high level of torsional stability. With a high level of torsional stability, racquets built in accordance with the present invention, provide exceptional control even on off-center hits.

The three flex prototype racquets exhibited torsional deflection measurements under the racquet torsional stability test of 3.9 degrees for the Flex Prototype 3, and 4.9 degrees for the Flex Prototype 2 and the Flex Prototype 1 prototype racquets. The deflection measurements from the racquet torsional stability test for the three flex prototype racquets are less than 5.5 degrees and less than 5.0 degrees. The average torsional stability measurement under the racquet torsional stability test for the 19 existing prior art racquets is 4.4 degrees, which is within 0.5 degrees above and below the three prototype flex racquets.

Racquets built in accordance with the present invention can exhibit advantageously low vibration characteristics providing lower shock and vibrational energy and an improved feel for the user. A modal analysis was performed on the three prototype racquets built in accordance with implementations of the present invention (the Flex Prototype 1, the Flex Prototype 3 and the Flex Prototype 2) and the 19 existing prior art racquets. Referring to FIG. 18, the modal analysis utilizes a model analysis system 180 including a computer or processor 182, a memory 184, a signal analyzer 186, a hammer 188, an accelerometer 189 and a modal analysis frame 190. The modal analysis system 180 includes modal analysis software code, such as STAR Modal Software provided by Spectral Dynamics, Inc. of San Jose, Calif. The signal analyzer 186 can be a Cougar Dynamic Signal Analyzer also provided by Spectral Dynamics, Inc. The modal analysis frame 190 allows for the racquet 10 to be suspended in a free-free condition such as through the use of rubber bands 191. In other implementations, the modal analysis frame can be other structures or supports that allow for a free-free suspension of the racquet for modal analysis. The accelerometer 189 is removably attached to the frame 12 of the racquet 10. Each racquet 10 was suspended in a free-free condition in the modal analysis frame 190 and acceleration measurements from the accelerometer 189 were taken using the hammer 188, which is impacted against the racquet 10 at the multiple testing positions about the racquet 10. The accelerometer 189 senses the vibration from the hammer impacts and sends a signal to the signal analyzer 186. The signal analyzer 186 is operably connected to the processor 182 and the memory 184. The modal analysis provides a vibration frequency value for the racquet 10.

The modal analysis vibration results as shown in Table 2 below demonstrate that the racquets built in accordance with implementations of the present invention provide significantly lower frequency values than the 19 existing prior art racquets. Racquets produced in accordance with implementations of the present invention exhibit frequency values that are lower than 140 Hz. In other implementations of the present invention, racquets 10 exhibit a frequency value that is less than 135 Hz. In other implementations of the present invention, racquets 10 exhibit a frequency value that is less than 130 Hz. In other implementations of the present invention, racquets 10 exhibit a frequency value that is less than 125 Hz. In other implementations of the present invention, racquets 10 exhibit a frequency value that is less than 120 Hz. In other implementations of the present invention, racquets 10 exhibit a frequency value that is less than 115 Hz. In other implementations of the present invention, racquets 10 exhibit a frequency value that is less than 110 Hz. The modal analysis of the three flex prototype racquets demonstrated racquet frequency values of 114 Hz, 115 Hz and 127 Hz, all of which are significantly lower than the 19 existing prior art racquets also measured under modal analysis. The frequency values of the 19 existing, prior art racquets range from 140 Hz to 191 Hz, which are 10 to 36 percent higher than the highest frequency value of the three flex prototype values (the Flex Prototype 2). The frequency values of the 19 existing, prior art racquets are at least 21 to 66 percent higher than frequency values of the remaining two flex prototype racquets. The significantly lower frequency values of the racquets built in accordance with implementations of the present invention can result in racquets that provide improved feel for user, and help to reduce player fatigue over time.

TABLE 2

RACQUET FREQUENCY RESULTS FROM MODAL ANALYSIS

| RACQUET MODEL | FREQUENCY (Hz) |
| --- | --- |
| Flex Prototype 2 | 115.0 |
| Flex Prototype 3 | 127.0 |
| Flex Prototype 1 | 114.0 |
| Wilson Ultra 2 MP | 183.0 |
| Wilson PS 5.5 SI | 153.0 |
| Wilson Profile Comp | 177.0 |
| Head Radical Tour | 155.0 |
| Prince Graphite MP | 159.0 |

TABLE 2-continued

RACQUET FREQUENCY RESULTS FROM MODAL ANALYSIS

| RACQUET MODEL | FREQUENCY (Hz) |
| --- | --- |
| Prince Tour 100 | 142.0 |
| Wilson Sting | 140.0 |
| Wilson Ultra 2 | 171.0 |
| Wilson Ultra 85 | 155.0 |
| Wilson Aggressor | 140.0 |
| Wilson Galaxy | 156.0 |
| Wilson Profile | 199.0 |
| Wilson Hammer 6.2 | 191.0 |
| Babolat Aero | 165.0 |
| Babolat Pure Drive | 177.0 |
| Head Radical mp | 166.0 |
| Wilson Ultra 100 | 172 |
| Wilson Blade 98 | 164 |

The incorporation of the present invention significantly improves the racquet's performance by increasing the lateral and forward/rearward flexibility of the racquet while maintaining a high level of torsional stability. Racquets built in accordance with the present invention provide a racquet with better feel and increased dwell time for the player, particularly for players who seek to impart a topspin onto a ball during play. Racquets built in accordance with the present invention address the lateral load that is applied to the racquet during the performance of a topspin swing and flex to improve the playability and performance of the racquet during such topspin swings. The present invention provides a racquet with increased lateral flexibility, increased forward/rearward flexibility and reduced levels of racquet vibration while maintaining high levels of torsional stability. Racquets built in accordance with the present invention improve the playability and performance of the racquet without requiring a significantly larger head size negatively affecting the moment of inertia of the racquet. The result is a significantly improved racquet that is particularly suited for highly skilled players.

While the preferred implementations of the present invention have been described and illustrated, numerous departures therefrom can be contemplated by persons skilled in the art. Therefore, the present invention is not limited to the foregoing description but only by the scope and spirit of the appended claims.

What is claimed is:

1. A tennis racquet extending along a longitudinal axis and capable of being tested under a racquet lateral bending test and a racquet forward/rearward bending test, wherein the racquet lateral bending test includes mounting the racquet in a first orientation to a first test fixture at a first longitudinal location, attaching a clamp to the racquet at a second location, operably engaging a deflection indicator to the clamp, applying a first predetermined weight to the racquet at a third location, and removing the first weight to obtain a lateral deflection measurement of the racquet with respect to the longitudinal axis, and wherein the racquet forward/rearward bending test includes mounting the racquet in a second orientation to the first test fixture at the first longitudinal location, applying a second predetermined weight to the racquet at a fourth location, operably engaging the deflection indicator to the racquet at a fifth location, and removing the second weight to obtain a forward/rearward deflection measurement with respect to the longitudinal axis, wherein the racquet is rotated 90 degrees about the longitudinal axis from the first orientation to the second orientation, the racquet comprising:

a frame including a head portion, a handle portion, and a throat portion positioned between the head portion and the handle portion, the head portion forming a hoop that defines a string bed plane, the throat portion including a pair of throat elements, at least the head portion and the throat portion of the racquet being formed at least in part of a fiber composite material, wherein, when the racquet is tested under the racquet lateral bending test, the racquet has a lateral deflection of at least 6.0 mm when measured in a direction that is parallel to the string bed plane and perpendicular to the longitudinal axis.

2. The sports racquet of claim 1, wherein, when the racquet is tested under the racquet forward/rearward bending test, the racquet has a forward/rearward deflection with respect to the longitudinal axis of at least 8.5 mm when measured in a direction that is perpendicular to the string bed plane and perpendicular to the longitudinal axis.

3. The tennis racquet of claim 2, wherein, when the racquet is tested under the racquet lateral bending test, the racquet has a lateral deflection of at least 6.5 mm when measured in a direction that is parallel to the string bed plane and perpendicular to the longitudinal axis.

4. The tennis racquet of claim 2, wherein, when the racquet is tested under the racquet lateral bending test, the racquet has a lateral deflection of at least 7.0 mm when measured in a direction that is parallel to the string bed plane and perpendicular to the longitudinal axis.

5. The tennis racquet of claim 2, wherein, when the racquet is tested under the racquet forward/rearward bending test, the racquet has a forward/rearward deflection with respect to the longitudinal axis of at least 9.0 mm when measured in a direction that is perpendicular to the string bed plane and perpendicular to the longitudinal axis.

6. The tennis racquet of claim 2, wherein, when the racquet is tested under the racquet forward/rearward bending test, the racquet has a forward/rearward deflection with respect to the longitudinal axis of at least 10.0 mm when measured in a direction that is perpendicular to the string bed plane and perpendicular to the longitudinal axis.

7. The tennis racquet of claim 1, wherein, when the racquet is tested under the racquet lateral bending test, the racquet has a lateral deflection of at least 6.5 mm when measured in a direction that is parallel to the string bed plane and perpendicular to the longitudinal axis.

8. The tennis racquet of claim 1, wherein, when the racquet is tested under the racquet lateral bending test, the racquet has a lateral deflection of at least 7.0 mm when measured in a direction that is parallel to the string bed plane and perpendicular to the longitudinal axis.

9. The tennis racquet of claim 1, wherein the racquet is capable of being tested under a racquet torsional stability test, wherein the racquet torsional stability test includes mounting the racquet to second and third test fixtures at sixth and seventh locations of the racquet, respectively, placing a third predetermined weight on an arm extending from the second test fixture to place a torsional load on to the racquet, removing the third predetermined weight to obtain an angular deflection about the longitudinal axis, and wherein, when the racquet is tested under the racquet torsional stability test, the racquet has an angular deflection of less than 5.5 degrees about the longitudinal axis.

10. The tennis racquet of claim 9, wherein when the racquet is tested under the racquet torsional stability test, the racquet has an angular deflection of no more than 5.0 degrees about the longitudinal axis.

11. The tennis racquet of claim 1, wherein the fiber composite material includes a plurality of ply arrangements, wherein each of the ply arrangements includes a pair of plies with one ply having a first plurality of fibers defining a first angle with respect to a composite axis and the other ply having a second plurality of fibers defining a second angle with respect to the composite axis, wherein the first and second angles are substantially the same except the first and second angles have opposite angular polarities with respect to the composite axis, wherein the head portion includes at least three ply arrangements overlaying each other, and wherein the first and second angles of at least two of the at least four ply arrangements are at least 35 degrees.

12. The tennis racquet of claim 11, wherein the first and second angles of at least two of the at least three ply arrangements are at least 40 degrees.

13. The tennis racquet of claim 11, wherein the first and second angles of at least two of the at least three ply arrangements are at least 45 degrees.

14. The tennis racquet of claim 1, wherein the head portion includes a forward hoop surface and a rearward hoop surface, wherein the distance between the forward and rearward hoop surfaces is a beam height distance, and wherein the head portion has a maximum beam height distance of at least 19 mm.

15. The tennis racquet of claim 1, wherein the racquet is capable of being tested in a racquet vibration test, wherein the racquet vibration test utilizes a modal analysis system including a hammer, an accelerometer and a modal analysis frame for supporting the racquet in a free-free condition during modal analysis, and wherein, when the racquet is tested under the racquet vibration test, the racquet has a vibration of no greater than 130 Hz.

16. A tennis racquet extending along a longitudinal axis and capable of being tested under a racquet lateral bending test and a racquet forward/rearward bending test, wherein the racquet lateral bending test includes mounting the racquet in a first orientation to a first test fixture at a first longitudinal location, attaching a clamp to the racquet at a second location, operably engaging a deflection indicator to the clamp, applying a first predetermined weight to the racquet at a third location, and removing the first weight to obtain a lateral deflection measurement of the racquet with respect to the longitudinal axis, and wherein the racquet forward/rearward bending test includes mounting the racquet in a second orientation to the first test fixture at the first longitudinal location, applying a second predetermined weight to the racquet at a fourth location, operably engaging the deflection indicator to the racquet at a fifth location, and removing the second weight to obtain a forward/rearward deflection measurement with respect to the longitudinal axis, wherein the racquet is rotated 90 degrees about the longitudinal axis from the first orientation to the second orientation, the racquet comprising:

a frame including a head portion, a handle portion, and a throat portion positioned between the head portion and the handle portion, the head portion forming a hoop that defines a string bed plane, the head portion including a forward hoop surface and a rearward hoop surface, the distance between the forward and rearward hoop surfaces being a beam height distance, the head portion having a maximum beam height distance of at least 20 mm, the throat portion including a pair of throat elements, wherein, when the racquet is tested under the racquet lateral bending test, the racquet has a lateral deflection of at least 6.0 mm when measured in a direction that is parallel to the string bed plane and perpendicular to the longitudinal axis.

17. The sports racquet of claim 16, wherein, when the racquet is tested under the racquet forward/rearward bending test, the racquet has a forward/rearward deflection with respect to the longitudinal axis of at least 8.5 mm when measured in a direction that is perpendicular to the string bed plane and perpendicular to the longitudinal axis.

18. The tennis racquet of claim 17, wherein, when the racquet is tested under the racquet lateral bending test, the racquet has a lateral deflection of at least 6.5 mm when measured in a direction that is parallel to the string bed plane and perpendicular to the longitudinal axis.

19. The tennis racquet of claim 17, wherein, when the racquet is tested under the racquet lateral bending test, the racquet has a lateral deflection of at least 7.0 mm when measured in a direction that is parallel to the string bed plane and perpendicular to the longitudinal axis.

20. The tennis racquet of claim 17, wherein, when the racquet is tested under the racquet forward/rearward bending test, the racquet has a forward/rearward deflection with respect to the longitudinal axis of at least 10.0 mm when measured in a direction that is perpendicular to the string bed plane and perpendicular to the longitudinal axis.

21. The tennis racquet of claim 16, wherein, when the racquet is tested under the racquet lateral bending test, the racquet has a lateral deflection of at least 6.5 mm when measured in a direction that is parallel to the string bed plane and perpendicular to the longitudinal axis.

22. The tennis racquet of claim 16, wherein, when the racquet is tested under the racquet lateral bending test, the racquet has a lateral deflection of at least 7.0 mm when measured in a direction that is parallel to the string bed plane and perpendicular to the longitudinal axis.

23. The tennis racquet of claim 16, wherein the racquet is capable of being tested under a racquet torsional stability test, wherein the racquet torsional stability test includes mounting the racquet to second and third test fixtures at sixth and seventh locations of the racquet, respectively, placing a third predetermined weight on an arm extending from the second test fixture to place a torsional load on to the racquet, removing the third predetermined weight to obtain an angular deflection about the longitudinal axis, and wherein, when the racquet is tested under the racquet torsional stability test, the racquet has an angular deflection of less than 5.5 degrees about the longitudinal axis.

\* \* \* \* \*